US011969477B2

(12) United States Patent
Sun

(10) Patent No.: US 11,969,477 B2
(45) Date of Patent: Apr. 30, 2024

(54) APPLICATION OF AUCS OR SUBSTANCES CONTAINING AUCS IN THE PREPARATION OF DRUGS FOR PREVENTING AND/OR TREATING GLAUCOMA

(71) Applicant: Shenzhen Profound-View Pharma Tech Co., Ltd, Shenzhen (CN)

(72) Inventor: Taolei Sun, Wuhan (CN)

(73) Assignee: Shenzhen Profound-View Pharma Tech Co., Ltd, Shenzhen (CN)

( * ) Notice: Subject to any disclaimer, the term of this patent is extended or adjusted under 35 U.S.C. 154(b) by 4 days.

(21) Appl. No.: 17/809,554

(22) Filed: Jun. 28, 2022

(65) Prior Publication Data
US 2022/0323608 A1  Oct. 13, 2022

Related U.S. Application Data

(62) Division of application No. 16/327,322, filed as application No. PCT/CN2017/113112 on Nov. 27, 2017, now Pat. No. 11,413,355.

(51) Int. Cl.
| | | |
|---|---|---|
| A61P 27/02 | (2006.01) | |
| A61K 31/28 | (2006.01) | |
| A61K 33/242 | (2019.01) | |
| A61K 47/54 | (2017.01) | |
| A61K 47/64 | (2017.01) | |
| A61K 47/69 | (2017.01) | |
| A61P 27/06 | (2006.01) | |

(52) U.S. Cl.
CPC .......... *A61K 47/6929* (2017.08); *A61K 31/28* (2013.01); *A61K 33/242* (2019.01); *A61K 47/54* (2017.08); *A61K 47/542* (2017.08); *A61K 47/64* (2017.08); *A61K 47/69* (2017.08); *A61P 27/02* (2018.01); *A61P 27/06* (2018.01)

(58) Field of Classification Search
None
See application file for complete search history.

(56) References Cited

U.S. PATENT DOCUMENTS

2015/0366882 A1* 12/2015 Altschul .............. B65D 75/367
514/19.5

OTHER PUBLICATIONS

Gautier, C, JAmChemSoc, 2006, 128, 11079-11087 (Year: 2006).*
N. Gao, H. Sun, K. Dong, J. Ren, X. Qu, Chemistry—A European Journal 2015, 21, 829.
H.F. Qian, M.Z. Zhu, Z.K. Wu, R.C. Jin, Accounts of Chemical Research 2012, 45, 1470.
V. Venkatesh, A. Shukla, S. Sivakumar, S. Verma, ACS Applied Materials & Interfaces 2014, 6, 2185.
C. Gautier, T. Burgi, Journal of the American Chemical Society 2006, 128,11079.
G. Li, R. C. Jin, Accounts of Chemical Research 2013, 46, 1749.
J. F. Parker, C. A. Fields-Zinna, R. W. Murray, Accounts of Chemical Research 2010, 43, 1289.
S. H. Yau, O. Varnavski, T. Goodson, Accounts of Chemical Research 2013, 46, 1506.
W. Yan, L. Xu, C. Xu, W. Ma, H. Kuang, L. Wang and N. A. Kotov, Journal of the American Chemical Society 2012, 134, 15114.
X. Yuan, B. Zhang, Z. Luo, Q. Yao, D. T. Leong, N. Yan and J. Xie, Angewandte Chemie International Edition 2014, 53, 4623.

* cited by examiner

*Primary Examiner* — Celeste A Roney
(74) *Attorney, Agent, or Firm* — Yihe Intellectual Property Service Company, Ltd

(57) ABSTRACT

Disclosed is the use of a gold cluster or a gold cluster-containing substance in the preparation of a drug for preventing and/or treating glaucoma.

6 Claims, 16 Drawing Sheets

(12) United States Patent

APPLICATION OF AUCS OR SUBSTANCES CONTAINING AUCS IN THE PREPARATION OF DRUGS FOR PREVENTING AND/OR TREATING GLAUCOMA

CROSS-REFERENCE TO RELATED APPLICATIONS

This application is a continuation application of U.S. patent application Ser. No. 16/327,322, filed Feb. 21, 2019, which is a continuation of International Application No. PCT/CN2017/113112, filed Nov. 27, 2017, which claims benefit of foreign priority to China patent application No. CN201611062360.X, filed Nov. 28, 2016; all of these applications are incorporated herein by reference.

FIELD OF THE INVENTION

The present invention relates to the technical field of nanometer drugs, particularly to the application of AuCs (gold clusters) or substances containing AuCs in the preparation of drugs for preventing and/or treating glaucoma.

BACKGROUND OF THE INVENTION

Glaucoma is an irreversible optic nerve degenerative disease characterized by optic nerve damage, visual field defect and gradual loss of visual function. It is the second irreversible blinding eye disease in the world after cataracts. It is forecast according to clinical analysis data that by 2020, the number of glaucoma patients in the world will reach 76 million, especially in Asia and Africa, while the number of glaucoma patients in China will reach 21 million by then. The pathogenesis of glaucoma remains unknown. For a long time, the elevation of pathological intraocular pressure is considered as one of the main factors causing nerve damage and glaucoma. The clinical treatment of glaucoma is mainly based on reducing the intraocular pressure of patients. However, enormous clinical data show that controlling intraocular pressure alone cannot achieve the goal of curing glaucoma. It is because even if the control on intraocular pressure is ideal, the progressive optic nerve damage and retinal ganglion cells (RGCs) apoptosis may still get worse. Therefore, high intraocular pressure may be only an early predisposing factor for glaucoma-related optic nerve damage, while it is difficult to prevent further loss of optic nerve function only by reducing intraocular pressure. For the above reasons, the key to the cure of glaucoma is to enhance optic nerve function, block or slow optic nerve cell apoptosis and optic nerve damage. However, no clinical drugs have been found to effectively prevent glaucoma-related optic nerve damage currently. Studies have found that a variety of factors can lead to optic nerve damage, such as oxidative stress, mechanical stress, autoimmune system abnormality, blood sugar level, inflammatory molecules and abnormal protein precipitation etc. Among the factors, more attention is paid to the misfolding, abnormal aggregation and fibrosis of amyloid-β (Aβ), and Tau protein inside and outside cells play crucial roles in the process of optic nerve degenerative disease and the death of RGCs.

Aβ is a protein that contains 39-43 amino acid residues, and generated from the hydrolysis of amyloid precursor protein (APP) by β-secretase and γ-secretase. It is an important factor involving in nerve damage and nerve cell apoptosis. Studies have shown that the neurotoxicity of Aβ is a common mechanism for the formation and pathogenesis of various neurodegenerative diseases, such as Alzheimer's disease (AD), and it has been used as an important target for the research and development of related drugs in a long time. Studies in recent years have shown that neurotoxicity of Aβ also plays a crucial role in ophthalmic neurodegenerative disease—glaucoma. The expression of Aβ in RGCs and aqueous humor of clinical glaucoma patients is significantly higher than the control group. In the glaucoma animal model, RGCs apoptosis induced by long-term high intraocular pressure is closely related to the increase of amyloid precursor protein (APP), Aβ expression and excessive hyperphosphorylation of Tau protein. Meanwhile, clinical data show that AD patients are easier to have glaucoma and vision loss. And a large quantity of APP is synthesized and Aβ plaque aggregation appears in the retina of AD transgenic animals. Therefore, glaucoma and AD may have similar Aβ mechanisms. More importantly, in the glaucoma animal model, RGCs in apoptotic phase are co-expressed with Aβ, and Aβ antibody or drugs which can block the overproduction of Aβ can effectively inhibit RGCs apoptosis and reduce optic nerve damage. These research results have shown that Aβ plays an important role in the pathogenesis of glaucoma and is an important target for the treatment of glaucoma based on optic nerve protection mechanism.

The optic nerve crush injury rat model is a widely-used animal model of glaucoma without high intraocular pressure. It maintains the integrity of the optic nerve epineurium, simulates the optic nerve axoplasmic transport disruption and RGCs death of glaucoma, which is close to the clinical glaucoma damage characteristics. At the same time, the model is prepared in a standard way and easy to operate, which can cause clear and quantitative optic nerve damage with small error and good repeatability. It is an accurate model for optic nerve damage of glaucoma, which is well recognized at home and abroad, and widely used in the studies of the pathological mechanisms of optic nerve damage and RGCs injury of glaucoma and the screening of drugs for optic nerve protection. For example, from this model, it has been found that ginsenoside Rg1, dexamethasone, ginkgo, and α-lipoic acid have some optic nerve protective effects, but the protective effects are not satisfactory. Since Aβ mechanism plays an important role in the optic nerve damage process, the development of a drug that can inhibit Aβ aggregation and fibrosis while protecting the optic nerve and improving visual function in animal model will have great significance to the prevention and treatment of glaucoma.

Gold nanoparticles are nanoscale gold particles (the diameter of the gold cores is 3-100 nm in general). Because of their unique optical and electric properties, good biocompatibility as well as convenient surface modification, gold nanoparticles are widely used in biology and related medical fields such as biosensors, medical imaging and tumor detection. Due to their chemical inertness and large specific surface area and the ability to penetrate the blood-brain barrier at low concentrations, gold nanoparticles are also used as drug carriers in the research of directional transport and controllable release of drugs, etc. In the recent years, research is made on binding gold nanoparticles with specific ligands (such as heteropolyacids and specific sequence polypeptides) that inhibit the aggregation of fibrotic proteins, achieving certain effects in vitro protein fibrosis inhibition experiments, but the results of the cell model indicate that the use of gold nanoparticles does not have an obvious effect on the survival rate of fibrin damaged cells (Literature 1: N. Gao, H. Sun, K. Dong, J. Ren, X. Qu, Chemistry-A European Journal 2015, 21, 829). No experiment at the level of animal model has been reported yet. Moreover, in these researches, gold nanoparticles were mainly used as drug carriers other than as active ingredients.

Gold clusters (AuCs) are ultrafine gold nanoparticles with a gold core less than 3 nm in diameter. It contains only a few to hundreds of gold atoms, causing the face-centered cubic packing structure of the gold atoms in the conventional gold nanoparticles to collapse and the energy level to split, thus showing molecule-like properties that are completely different from the conventional gold nanoparticles of above 3 nm: On the one hand, due to energy level splitting, AuCs do not possess the surface plasmon effect and derived optical properties of conventional gold nanoparticles, but exhibit excellent fluorescence emission properties similar to semiconductor quantum dots. On the other hand, in the ultraviolet-visible absorption spectrum of AuCs, the plasmon resonance peak at 520±20 nm disappears, while one or more new absorption peaks appear above 570 nm, and such absorption peaks cannot be observed in conventional gold nanoparticles. Therefore, the disappearance of the plasmon resonance absorption peak (520±20 nm) and the appearance of the new absorption peaks above 570 nm in the UV-visible absorption spectrum are important indicators for judging whether AuCs are successfully prepared (Literature 2: H. F. Qian, M. Z. Zhu, Z. K. Wu, R. C. Jin, Accounts of Chemical Research 2012, 45, 1470). AuCs also have magnetic, electrical and catalytic properties that are significantly different from those of conventional gold nanoparticles, so they have broad application prospects in the fields of single-molecule optoelectronics, molecular catalysis. In addition, AuCs have also been used in the fields of bioprobes and medical imaging due to their excellent fluorescence emission properties. For example, Sandeep Verma team uses purine-modified AuCs as green fluorescent probes for nucleus imaging (Literature 3: V. Venkatesh, A. Shukla, S. Sivakumar, S. Verma, ACS Applied Materials & Interfaces 2014, 6, 2185). This type of literatures utilizes the fluorescence properties of AuCs and does not relate to the medicinal activity of AuCs themselves.

SUMMARY OF THE INVENTION

The object of the present invention is to provide a medical use of AuCs, and specifically to provide a new application thereof in the preparation of drugs for preventing and treating glaucoma.

In the first aspect, the present invention provides an application of substances containing AuCs in the preparation of drugs for preventing and/or treating glaucoma.

The substances containing AuCs comprise AuCs and ligand Y that coats AuCs externally.

The substances containing AuCs are solution, powder or floc.

The gold core diameter of the AuCs is smaller than 3 nm.

The gold core diameter of the AuCs is 0.5-2.6 nm or 1.1-2.6 nm.

The ligand Y includes without limitation one or more of L(D)-cysteine and its derivatives, oligopeptides containing cysteine and their derivatives, and other compounds containing thiol.

The L(D)-cysteine and its derivatives are preferably L(D)-cysteine, N-isobutyryl-L(D)-cysteine (L(D)-NIBC) or N-acetyl-L(D)-cysteine (L(D)-NAC).

The oligopeptides containing cysteine and their derivatives are selected from L-arginine-L-cysteine (RC), L-cysteine-L-arginine (CR), L-cysteine-L-histidine dipeptide (CH), L-histidine-L-cysteine dipeptide (HC), L-glutathione (GSH), L-lysine-L-cysteine-L-proline tripeptide (KCP), L-proline-L-cysteine-L-arginine tripeptide (PCR), glycine-L-cysteine-L-arginine tripeptide (GCR), glycine-L-serine-L-cysteine-L-arginine tetrapeptide (GSCR) or glycine-L-cysteine-L-serine-L-arginine tetrapeptide (GCSR).

Other compounds containing thiol are selected from 1-[(2S)-2-methyl-3-thiol-1-oxopropyl]-L-proline (Cap), thioglycollic acid, mercaptoethanol, thiophenol, D-3-trolovol, N-(2-mercaptopropionyl)-glycine or dodecyl mercaptan, etc.

A method for preparing the substances containing AuCs comprises the following steps:

(1) $HAuCl_4$ is dissolved in one of methanol, water, ethanol, n-propanol and ethyl acetate, a solution A is obtained, where the concentration of $HAuCl_4$ is 0.01~0.03 M;

(2) Ligand Y is dissolved in a solvent to obtain a solution B, where the concentration of ligand Y is 0.01~0.18 M;

(3) The solution A in step (1) and the solution B in step (2) are mixed, where the mole ratio of $HAuCl_4$ and ligand Y is 1:0.01~1:100 (preferably 1: (0.1-10), more preferably 1: (1-10)), and the mixture is stirred in an ice bath for 0.1~12 h (preferably 0.1-2h, more preferably 0.5-2 h); 0.025~0.8 M solution of $NaBH_4$ (preferably water solution of $NaBH_4$, ethanol solution of $NaBH_4$ or methanol solution of $NaBH_4$) is added dropwise, and then the reaction system is stirred in an ice bath for 0.1~12 h (preferably 0.1-2 h, more preferably 1-2 h), where the mole ratio of $NaBH_4$ and ligand Y is 1:0.01~1:100 (preferably 1:(0.1-8), more preferably 1:(1-8)) to obtain the solution-like substances containing AuCs The solvent in step (2) is one or more of methanol, ethyl acetate, water, ethanol, n-propanol, pentane, formic acid, acetic acid, diethyl ether, acetone, anisole, 1-propanol, 2-propanol, 1-butanol, 2-butanol, pentanol, ethanol, butyl acetate, tributyl methyl ether, isopropyl acetate, dimethyl sulfoxide, ethyl acetate, ethyl formate, isobutyl acetate, methyl acetate, 2-methyl-1-propanol and propyl acetate.

The solution-like substances containing AuCs obtained in step (3) are dialyzed, freeze-dried, then a powdery or flocculant substances containing AuCs are obtained; preferably, the dialysis is that the solution-like substances containing AuCs are put in a dialysis bag and dialyzed in water at room temperature for 1~7 days.

In the second aspect, the present invention provides an application of AuCs in the preparation of drugs for preventing and/or treating glaucoma. The gold core diameter of the AuCs is less than 3 nm. The AuCs may be modified with different ligands, which may be ingredients effective or ineffective to glaucoma.

In the third aspect, the present invention provides an application of AuCs modified with ligand of L-NIBC, D-NIBC, CR, RC, N-acetyl-L-cysteine (L-NAC), N-acetyl-D-cysteine (D-NAC), GSH, 1-[(2S)-2-methyl-3-thiol-1-oxopropyl]-L-proline (Cap), L-cysteine or D-cysteine in the preparation of drugs for preventing and/or treating glaucoma.

The gold core diameter of the AuCs is smaller than 3 nm, preferably 0.5-2.6 nm.

The AuCs or substances containing AuCs (referring to ligand-modified AuCs) provided in the present invention may be administered by oral, injection (intramuscular or intravenous injection) or local eye dropping. The dosage and frequency of administration can be calculated according to the results of cell model experiments, animal model experiments, drug in-vivo distribution and metabolic experiments.

In terms of efficacy, the AuCs or substances containing AuCs provided in the present invention show an excellent effect on inhibiting Aβ aggregation in an in vitro experiment of Aβ aggregation inhibition and a significant effect on improving cell survival rate in the RGC-5 optic ganglion cell injury model. In the rat glaucoma optic nerve clamping injury model, they may significantly increase the N2-P2 amplitude of the flash visual evoked potentials in optic nerve crush injury model rats and significantly reduce the loss of RGCs. They have obvious protective effect on optic nerve damage, can reduce the visual field defect and the RGCs apoptosis, and have a remarkable function on improving the structure of retina and optic nerve tissue and alleviating visual dysfunction. Moreover, they are of great biocompatibility at the animal level. Therefore, it is significant to the research and development of new drugs for preventing and treating glaucoma.

At the same time, the present invention also demonstrates that the ligand molecules themselves do not have an obvious effect in the kinetic experiment of Aβ aggregation inhibition in vitro and the glaucoma cell model of RGC-5 cell injury, which indicates that the efficacy on glaucoma comes from AuCs rather than ligands. The new medical use of AuCs is an important contribution of the present invention. Based on their medicinal activity of AuCs to glaucoma, if AuCs are further combined with known active substances (including but not limited to the activity to glaucoma) or other inactive substances such as carriers and cosolvents, more competitive new drugs will be formed.

DETAILED DESCRIPTION OF THE EMBODIMENTS

Figure 1:
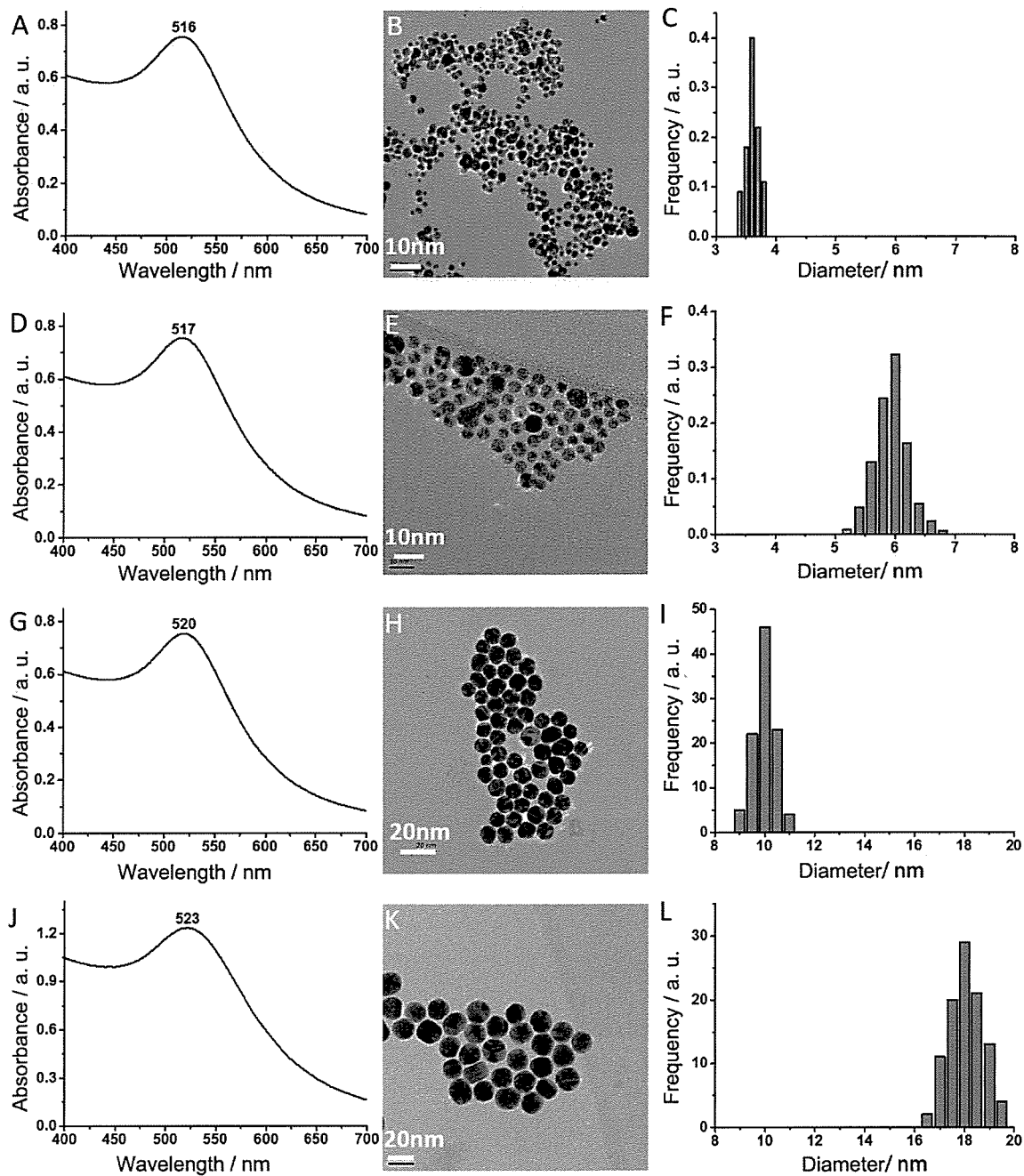
FIG. 1 shows ultraviolet-visible (UV) spectrums, transmission electron microscope (TEM) images and particle size distribution diagrams of ligand L-NIBC-modified gold nanoparticles with different particle sizes.

When studying the effect of gold nanoparticles (gold core diameter 3 nm-100 nm) with certain ligands on Aβ aggregation, the inventors found that when the gold core diameter of gold nanoparticles was changed from large to small, the promoting effect of gold nanoparticles modified with the same ligand on their surfaces on Aβ aggregation was converted into inbibitory one; when the particle size was small enough to become gold clusters (AuCs) (gold core diameter is less than 3 nm), complete inhibition of Aβ aggregation could be achieved. In this effect, it is AuCs themselves other than ligands to play an inhibitory role.

Generally, the gold core diameter of the gold nanoparticles used in the research is greater than 3 nm, and when the diameter of the gold core is smaller than 3 nm, they are called gold clusters (AuCs). The disappearance of plasmon resonance absorption peak (520±20 nm) and the appearance of new absorption peaks above 560 nm or 570 nm in UV-visible absorption spectrum are the characteristics indicating whether the AuCs are prepared successfully. Without ligands, AuCs cannot exist stably in a solution. It combines with thiol-containing ligand to form ligand-modified AuCs (or called AuCs) via Au—S bond.

The existing ligand-modified AuCs disclosed in the literature include AuCs modified with L-glutathione (GSH), N-acetyl-L(D)-cysteine (L(D)-NAC), N-isobutyryl-L(D)-cysteine (L(D)-NIBC), etc. The preparation process is shown in the literatures (Literature 4: H. F. Qian, M. Z. Zhu, Z. K. Wu, R. C. Jin, Accounts of Chemical Research 2012, 45, 1470; Literature 5: C. Gautier, T. Bürgi, Journal of the American Chemical Society 2006, 128,11079); they are mainly applied in the fields of catalysis, chiral recognition, molecular detection, biosensing, drug delivery and bioimaging (Literature 6: G. Li, R. C. Jin, Accounts of Chemical Research 2013, 46, 1749; Literature 7: H. F. Qian, M. Z. Zhu, Z. K. Wu, R. C. Jin, Accounts of Chemical Research 2012, 45, 1470; Literature 8: J. F. Parker, C. A. Fields-Zinna, R. W. Murray, Accounts of Chemical Research 2010, 43, 1289; S. H. Yau, O. Varnayski, T. Goodson, Accounts of Chemical Research 2013, 46, 1506).

The present invention investigated the effects of AuCs on inhibition of Aβ aggregation, at least including: firstly, AuCs of different sizes containing different ligands (the ligands not having inhibitory effect on Aβ aggregation) were used as research objects. Through research at three levels of experiments, including in vitro experiments for inhibition of Aβ aggregation, RGC-5 optic ganglion cell injury model experiment, optic nerve crush injury rat model, and in consideration of AuCs cytotoxicity, acute toxicity experiment in mice, in vivo distribution and pharmacokinetics experiment in mice, etc., ligand-modified AuCs were provided, their application in the preparation of drugs treating glaucoma was found, and the results were compared with the experimental results of gold nanoparticles, indicating that gold nanoparticles with a diameter of greater than 3 nm do not have a desirable effect for this purpose, and cannot be used to prepare drugs treating glaucoma, while ligand-modified AuCs can be used to prepare drugs treating glaucoma.

Hereunder the present invention will be further detailed in embodiments, but those embodiments should not be understood as constituting any limitation to the present invention.

The purity of the raw materials used in the following embodiments shall be chemical purity or higher. They all may be purchased from the market.

Embodiment 1: Prepare Ligand-Modified AuCs

This embodiment discloses a method for preparing ligand-modified AuCs(ligand-modified AuCs are also called substances containing AuCs in the present invention), said method comprising the following steps:

(1) Dissolving $HAuCl_4$ in one of methanol, water, ethanol, n-propanol and ethyl acetate to get a solution A in which the concentration of $HAuCl_4$ is 0.01~0.03 M;

(2) Dissolving ligand Y in a solvent to get a solution B in which the concentration of ligand Y is 0.01~0.18 M; ligand Y includes, but not limited to, L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), L-histidine-L-cysteine (HC), L-lysine-L-cysteine-L-proline (KCP), glycine-L-cysteine-L-arginine tripeptide (GCR), L-proline-L-cysteine-L-arginine tripeptide (PCR), L-glutathione (L-GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline (Cap), thioglycollic acid, mercaptoethanol, thiophenol, D-3-trolovol and dodecyl mercaptan; the solvent is one or more of methanol, ethyl acetate, water, ethanol, n-propanol, pentane, formic acid, acetic acid, diethyl ether, acetone, anisole, 1-propanol, 2-propanol, 1-butanol, 2-butanol, pentanol, ethanol, butyl acetate, tributyl methyl ether, isopropyl acetate, dimethyl sulfoxide, ethyl acetate, ethyl formate, isobutyl acetate, methyl acetate, 2-methyl-1-propanol and propyl acetate;

(3) Mixing solution A and solution B so that the mole ratio between $HAuCl_4$ and ligand Y is 1:(0.1~10), stirring them in an ice bath for 0.1~24 h, adding 0.025~0.8 M $NaBH_4$ solution in water, ethanol or methanol, continuing to stir in an ice water bath and react for 0.1~2 h. The mole ratio between $NaBH_4$ and ligand Y is 1:(0.1~8); then solution-like substances containing AuCs is obtained;

In order to obtain AuCs in different sizes, measure particle sizes and facilitate the usage, the following steps may be taken further:

(4) The solution obtained in step (3) is centrifuged at different speed in the range of 8,000~17,500 r/min by gradient for 10~100 min after the the reaction ends, the precipitates of ligand-modified AuCs in different average particle sizes under different rotational speed are obtained;

(5) Dissolving the AuCs precipitate in different average particle sizes obtained in step (4) in water, putting it in a dialysis bag and dialyzing it in water at room temperature for 1~7 days;

(6) Freeze-drying AuCs for 12~24 h after dialysis to obtain a powdery or flocculant substance, i.e., ligand-modified AuCs.

The obtained powdery or floccule substance (the specific detection method is shown in Embodiment 2) was characterizied. It was found that the particle size of the precipitates obtained through centrifuging at different rotational speeds was smaller than 3 nm (distributed in 0.5-2.6 nm in general). The UV-visible absorption spectrum has one or more absorption peaks above 570 nm, and no obvious absorption peak at 520 nm. It is determined that the obtained powder or floc is AuCs.

Embodiment 2: Preparation of AuCs with Ligand being N-isobutyryl-L-cysteine (L-NIBC)

Taking ligand L-NIBC for example in this embodiment, the preparation and confirmation of AuCs modified with ligand L-NIBC in different particle sizes are detailed.

(1) Weigh 1.00 g of $HAuCl_4$ and dissolve it in 100 mL of methanol to obtain a 0.03 M solution A;

(2) Weigh 0.57 g of L-NIBC and dissolve it in 100 mL of glacial acetic acid (acetic acid) to obtain a 0.03 M solution B;

(3) Measure 1 mL of solution A, mix it with 0.5 mL, 1 mL, 2 mL, 3 mL, 4 mL, 5 mL of solution B respectively (i.e. the mole ratio between $HAuCl_4$ and L-NIBC is 1:0.5, 1:1, 1:2, 1:3, 1:4, 1:5 respectively), react in an ice bath under stirring for 2 h, quickly add 1 mL of freshly prepared 0.03 M (prepared by weighing 11.3 mg of $NaBH_4$ and dissolving it in 10 mL of ethanol) $NaBH_4$ water solution when the solution turns colorless from bright yellow, continue the reaction for 30 min after the solution turns dark brown, and add 10 mL of acetone to terminate the reaction.

(4) After the reaction, the reaction solution is subjected to differential centrifugation (i.e., by gradient centrifugation) to obtain L-NIBC modified AuCs powder with different particle sizes. This step might be used in combination with an ultrafiltration tube, and specific method: After the reaction in step (3) is completed, the reaction solution is transferred to an ultrafiltration tube with MWCO of 100,000 and a volume of 50 mL, and centrifuged at 10000 r/min for 20 min, and the retentate precipitate in the tube was L-NIBC-modified AuCs powder with a particle size of about 2.6 nm (2.6 nm was measured by resuspending this retentate precipitate in ultrapure water).Then, the solution outside the tube is transferred to an ultrafiltration tube with a volume of 50 mL and MWCO of 50,000, and centrifuged at 13,000 r/min for 30 min. The retentate precipitate in the tube is L-NIBC-modified AuCs powder with a particle size of about 1.8 nm (1.8 nm was measured by resuspending this retentate precipitate in ultrapure water). Then the solution outside the tube is transferred to an ultrafiltration tube with a volume of 50 mL and MWCO of 30,000, and centrifuged at 17,500 r/min for 40 min. The retentate precipitate in the inner tube is L-NIBC-modified AuCs powder with a particle size of about 1.1 nm (1.1 nm was measured by resuspending this retentate precipitate in ultrapure water).

(5) The powder in three different particle sizes was obtained by gradient centrifugation, then removed the solvent respectively, crude product was obtained. The crude product was blow-dried with $N_2$, dissolved in 5 mL of ultrapure water, put in a dialysis bag (MWCO is 7,000 Da), then in 2 L ultrapure water. The water was changed every other day, and it was dialyzed for 7 days, freeze-dried and kept for future use Characterization experiment was conducted for the powder obtained above (ligand modified AuCs). Meanwhile, ligand L-NIBC modified gold nanoparticles are used as control. The method for preparing gold nanoparticles with ligand being L-NIBC refers to the reference (Literature 10: W. Yan, L. Xu, C. Xu, W. Ma, H. Kuang, L. Wang and N. A. Kotov, Journal of the American Chemical Society 2012, 134, 15114; X. Yuan, B. Zhang, Z. Luo, Q. Yao, D. T. Leong, N. Yan and J. Xie, Angewandte Chemie International Edition 2014, 53, 4623).

1. Observe the Morphology by Transmission Electron Microscope (TEM)

The test powders (L-NIBC modified AuCs sample prepared in Embodiment 2 and L-NIBC modified gold nanoparticle sample) were dissolved in ultrapure water to 2 mg/L as samples, and then test samples were prepared by hanging drop method. The specific method: 5 μL of the samples were dripped on an ultrathin carbon film, volatized naturally till the water drop disappeared, and then observe the morphology of the samples by JEM-2100F STEM/EDS field emission high-resolution TEM.

Figure 2:
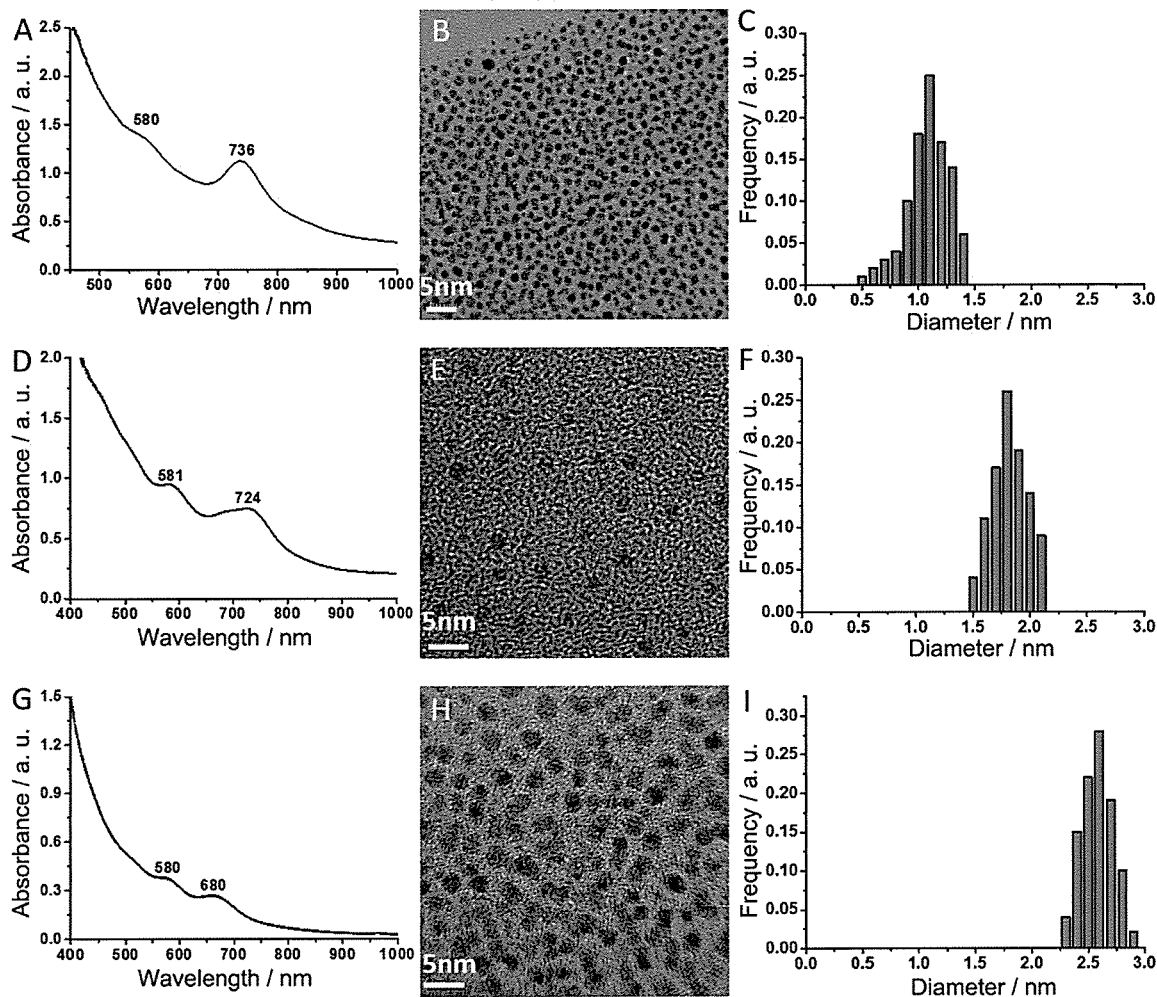
FIG. 2 shows ultraviolet-visible spectrums, TEM images and particle size distribution diagrams of ligand L-NIBC-modified AuCs with different particle sizes.

The four TEM images of ligand L-NIBC modified gold nanoparticles are shown in panels B, E, H, and K of FIG. 1; the three TEM images of ligand L-NIBC modified AuCs are shown in panels B, E, and H of FIG. 2.

The images in FIG. 2 indicate that the L-NIBC-modified AuCs samples have a uniform particle size and good dispersibility, and the average diameter of L-NIBC-modified AuCs (refer to the diameter of gold core) is 1.1 nm, 1.8 nm and 2.6 nm respectively, in good accordance with the results in panels C, F and I of FIG. 2. In comparison, ligand L-NIBC modified gold nanoparticle samples have a larger particle size. Their average diameter (refer to the diameter of gold core) is 3.6 nm, 6.0 nm, 10.1 nm and 18.2 nm respectively, in good accordance with the results in panels C, F, I and L of FIG. 1.

2. Ultraviolet (UV)-Visible (vis) Absorption Spectrum

The test powder was dissolved in ultrapure water till the concentration was 10 mg·$L^{-1}$, and was measured by UV-vis absorption spectrum at room temperature. The scanning range was 190-1100 nm, the sample cell was a standard quartz cuvette with an optical path of 1 cm, and the reference cell was filled with ultrapure water.

The UV-vis absorption spectra of the four ligand L-NIBC-modified gold nanoparticle samples with different sizes are shown in panels A, D, G and J of FIG. 1, and the statistical distribution of particle size is shown in panels C, F, I and L of FIG. 1; the UV-vis absorption spectra of three ligand L-NIBC modified AuCs samples with different sizes are shown in panels A, D and G of FIG. 2, and the statistical distribution of particle size is shown in panels C, F and I of FIG. 2.

FIG. 1 indicates that due to the surface plasmon effect, ligand L-NIBC modified gold nanoparticles had an absorption peak at about 520 nm. The position of the absorption peak is relevant with particle size. When the particle size is 3.6 nm, the UV absorption peak appears at 516 nm; when the particle size is 6.0 nm, the UV absorption peak appears at 517 nm; when the particle size is 10.1 nm, the UV absorption peak appears at 520 nm, and when the particle size is 18.2 nm, the absorption peak appears at 523 nm. None of the four samples has any absorption peak above 560 nm or 570 nm.

FIG. 2 indicates that in the UV absorption spectra of three ligand L-NIBC-modified AuCs samples with different particle sizes in Embodiment 2, the surface plasmon effect absorption peak at 520 nm disappeared, and two obvious absorption peaks appeared above 570 nm and the positions of the absorption peaks varied slightly with the particle sizes of AuCs. This is because AuCs exhibit molecule-like properties due to the collapse of the face-centered cubic structure, which leads to the discontinuity of the density of states of AuCs, the energy level splitting, the disappearance of plasmon resonance effect and the appearance of a new absorption peak in the long-wave direction. It could be concluded that the three powder samples in different particle sizes obtained in Embodiment 2 are all ligand-modified AuCs.

3. Fourier Transform Infrared Spectroscopy

Infrared spectra were measured on a VERTEX80V Fourier transform infrared spectrometer manufactured by Bruker in a solid powder high vacuum total reflection mode. The scanning range is 4000-400 $cm^{-1}$ and the number of scans is 64. Taking the L-NIBC modified AuCs samples prepared in Embodiment 2 for example, the test samples were L-NIBC modified AuCs dry powder with three different particle sizes and the control sample was pure L-NIBC powder. The results are shown in FIG. 3.

Figure 3:
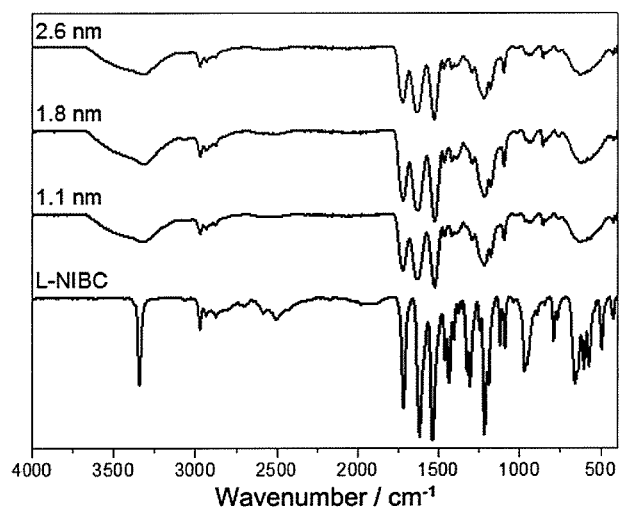
FIG. 3 shows infrared spectrums of ligand L-NIBC-modified AuCs with different particle sizes.

FIG. 3 shows the infrared spectrum of L-NIBC modified AuCs with different particle sizes. Compared with pure L-NIBC (the curve at the top), the S—H stretching vibrations of L-NIBC modified AuCs with different particle sizes all disappeared completely at 2500-2600 $cm^{-1}$, while other characteristic peaks of L-NIBC were still observed, proving that L-NIBC molecules were successfully anchored to the surface of AuCs via Au—S bond. The figure also shows that the infrared spectrum of the ligand-modified AuCs is irrelevant with its size.

4. Near Infrared Fluorescence Spectrum

The near infrared fluorescence spectrum was measured on a NanoLog ultraviolet-visible-near infrared fluorescence spectrometer produced by Horiba JobinYvon. The sample cell was a standard quartz cuvette with an optical path of 1 cm. The excitation wavelength was 415 nm and the slit width was 10 nm. The range of detected emission wavelength was 700-1,500 nm, and the slit width was 10 nm. Taking L-NIBC-modified AuCs samples in Embodiment 2 as an example, the results were shown in FIG. 4.

Figure 4:
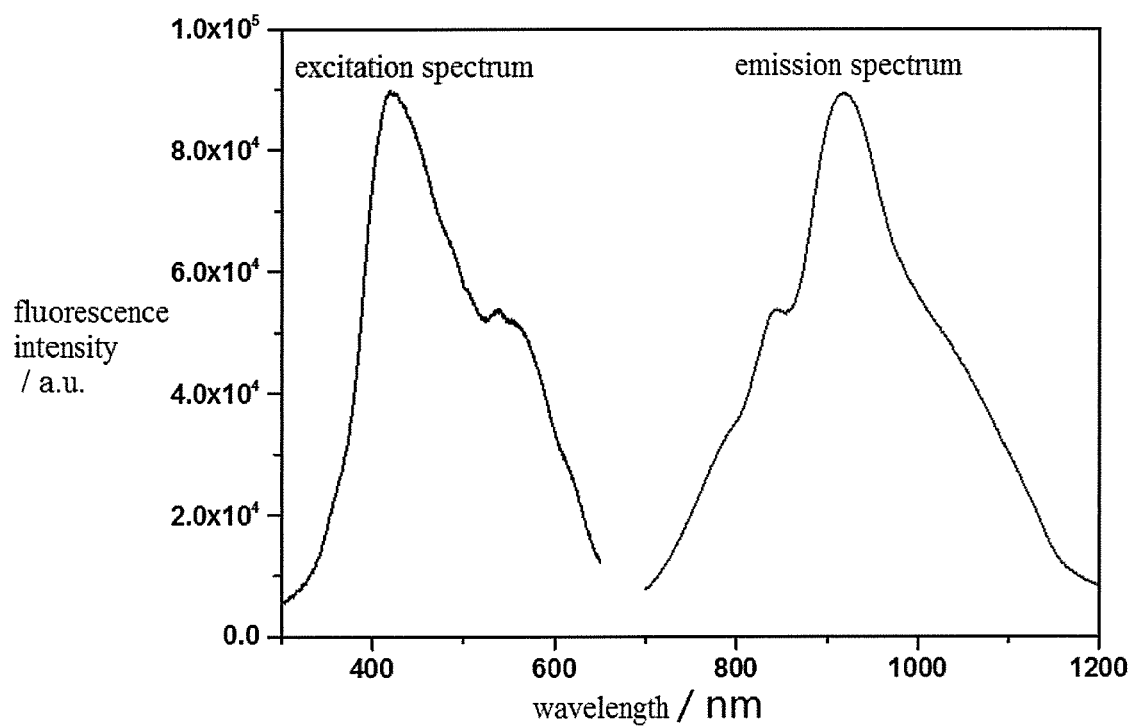
FIG. 4 shows excitation spectrums and near-infrared fluorescence emission spectrums of L-NIBC-modified AuCs in an average diameter of 1.8 nm.

FIG. 4 was an excitation spectrum and near-infrared fluorescence emission spectrum of L-NIBC-modified AuCs in an average diameter of 1.8 nm. It was found that due to energy level splitting, AuCs also exhibited fluorescence emission properties similar to semiconductor quantum dots. The AuCs of other particle sizes and ligands also had this property, but the peak positions of the excitation spectrum and emission spectrum varied slightly with ligands and particle sizes of AuCs. The gold nanoparticles with the same ligand did not have fluorescence emission characteristics in all bands.

AuCs modified by other ligand Y were prepared by a method similar to the above method, except that the solvent of solution B, the feed ratio between HAuCl$_4$ and ligand Y, the reaction time and the amount of NaBH$_4$ added were slightly adjusted. For example: when L-cysteine, D-cysteine, N-isobutyryl-L-cysteine (L-NIBC) or N-isobutyryl-D-cysteine (D-NIBC) is used as ligand Y, acetic acid is selected as the solvent; when dipeptide CR, dipeptide RC or 1-[(2S)-2-methyl-3-thiol-1-oxopropyl]-L-proline is used as ligand Y, water is selected as the solvent, and so on and so forth; other steps are similar, so they won't be described in details here.

The present invention prepared and obtained a series of ligand-modified AuCs by the foregoing method. The ligands and the parameters of the preparation process are shown in Table 1.

The results indicate that the diameters of AuCs modified with different ligands obtained from Table 1 are all smaller than 3 nm. Ultraviolet spectra also show disappearance of peak at 520±20 nm, and appearance of absorption peak above 560 nm (560 nm or 570 nm). Only the position of this absorption peak varies slightly with ligand and particle size. Meanwhile, Fourier transform infrared spectrum also shows disappearance of ligand thiol infrared absorption peak (between the dotted lines in panel B of FIG. 7-FIG. 11), while other infrared characteristic peaks are all retained, suggesting that all ligand molecules have been successfully anchored to the surface of AuCs, and the present invention has successfully obtained AuCs modified with the ligands listed in Table 1

TABLE 1

Preparation parameters of AuCs modified with different ligands

| Embodiments | Ligand Y | Solvent used for solution B | Feed ratio between HAuCl$_4$ and Y | Time of reaction in an ice bath under stirring before addition of NaBH$_4$ | Mole ratio between HAuCl$_4$ and NaBH$_4$ | Time of reaction in an ice bath under stirring after addition of NaBH$_4$ |
|---|---|---|---|---|---|---|
| 1 | L-cysteine | Acetic acid | 1:3 | 2 h | 1:2 | 0.5 h |
| 2 | D-cysteine | Acetic acid | 1:3 | 2 h | 1:2 | 0.5 h |
| 3 | N-acetyl-L-cysteine | Ethanol | 1:4 | 1 h | 1:1 | 0.5 h |
| 4 | N-acetyl-D-cysteine | Ethanol | 1:4 | 1 h | 1:1 | 0.5 h |
| 5 | L-NIBC | Water | 1:4 | 0.5 h | 1:2 | 0.5 h |
| 6 | D-NIBC | Water | 1:4 | 0.5 h | 1:2 | 0.5 h |
| 7 | Other cysteine derivatives | Soluble solvent | 1:(0.1~100) | 0.5 h~24 h | 1:(0.1~100) | 0.1~24 h |
| 8 | CR | Water | 1:4 | 22 h | 2:1 | 0.5 h |
| 9 | RC | Water | 1:4 | 20 h | 2:1 | 0.5 h |
| 10 | HC | Water | 1:3 | 12 h | 1:2 | 2 h |
| 11 | CH | Ethanol | 1:4 | 16 h | 1:3 | 3 h |
| 12 | GSH | Water | 1:2 | 12 h | 1:1 | 3 h |
| 13 | KCP | Water | 1:3 | 15 h | 1:2 | 1 h |
| 14 | PCR | Water | 1:4 | 16 h | 1:3 | 2 h |
| 15 | GCR | Water | 1:4 | 16 h | 1:3 | 3 h |
| 16 | GSCR | Water | 1:4 | 16 h | 1:3 | 1.5 h |
| 17 | GCSR | Water | 1:3 | 12 h | 1:2 | 2 h |
| 18 | Other peptides containing cysteine | Soluble solvent | 1:(0.1~100) | 0.5 h~24 h | 1:(0.1~100) | 0.1~24 h |
| 19 | 1-[(2S)-2-methyl-3-thiol-1-oxopropyl]-L-proline | Water | 1:8 | 2 h | 1:7 | 1 h |
| 20 | Mercaptoethanol | Ethanol | 1:2 | 2 h | 1:1 | 1 h |
| 21 | Thioglycollic acid | Acetic acid | 1:2 | 2 h | 1:1 | 1 h |
| 22 | Thiophenol | Ethanol | 1:5 | 5 h | 1:1 | 1 h |
| 23 | D-3-trolovol | Water | 1:2 | 2 h | 1:1 | 1 h |
| 24 | N-(2-mercaptopropionyl)-glycine | Water | 1:2 | 2 h | 1:1 | 1 h |
| 25 | Dodecyl mercaptan | Methanol | 1:5 | 5 h | 1:1 | 1 h |
| 26 | Other compounds containing thiol | Soluble solvent | 1:(0.01~100) | 0.5 h~24 h | 1:(0.1~100) | 0.1~24 h |

The samples in embodiments listed in Table 1 are confirmed by the foregoing method. FIG. 7-FIG. 11 are UV spectra (panel A in FIG. 7-FIG. 11), infrared spectra (panel B in FIG. 7-FIG. 11), transmission electron microscope (TEM) images (panel C in FIG. 7-FIG. 11) and particle size distribution (panel D in FIG. 7-FIG. 11) of AuCs modified with ligand CR, RC, 1-[(2S)-2-methyl-3-thiol-1-oxopropyl]-L-proline (abbreviation: Cap), GSH and D-NIBC.

Embodiment 3: In Vitro Aβ Aggregation Kinetic Experiment

As described above, Aβ plays an important role in the pathogenesis of glaucoma and is an important target for treatment of glaucoma based on the optic nerve protection mechanism. This embodiment investigated the functions of AuCs (ligand-modified AuCs) by in vitro experiment of Aβ aggregation kinetics, and compared the effects on Aβ aggregation kinetics with same ligand-modified gold nanoparticles and independent use of ligand molecules to prove that AuCs could complete inhibit Aβ aggregation, while gold nanoparticles did not have this function. Moreover, the function is from AuCs other than ligand. The experiment used ThT fluorescent labeling method to characterize the kinetics of Aβ(1-40) aggregation and fibrosis.

Thioflavin T (abbreviation: ThT) is a dye specifically for dyeing amyloid fibers. When it is incubated together with monomers of polypeptides or proteins, its fluorescence does not change substantially. When it encounters amyloid polypeptides or proteins with a fiber structure, it will immediately couple with the amyloid polypeptides or proteins and its fluorescence intensity will increase exponentially. Just because of this property, ThT is widely used as a marker to monitor amyloidosis of peptides or proteins. The fibrosis process of Aβ(1-40) is also a nucleation-controlled polymerization process. Therefore, the growth curve of Aβ(1-40) fiber measured by ThT fluorescent labeling method is mainly divided into three stages: Initial stage, growth stage and platform stage. The initial stage is mainly a stage when Aβ(1-40) undergoes conformational transition to form misfolding and then aggregates and nucleates. The growth stage is a stage when Aβ(1-40) monomers are accumulated onto the cores of oligomers along the axial direction to form fibers and grow rapidly. The platform stage is a stage when all Aβ(1-40) molecules form mature long fibers, i.e., a stage when the fibers no longer grow. ThT fluorescent labeling method can conveniently monitor the kinetics process of fibrotic aggregation of Aβ(1-40) molecules.

1) Pretreatment of Aβ(1-40) Monomers

Freeze-dried powder of amyloid polypeptide Aβ(1-40) (Invitrogen Corp.) was dissolved in hexafluoroisopropanol (HFIP) to obtain a 1 g/L Aβ(1-40) solution, and the solution was inculated at room temperature for 2-4 h after sealing, then blowed to dry HFIP (for about 1 h) with high-purity nitrogen (N2, 99.9%) at an appropriate flow rate in a fume hood. Lastly the dried Aβ(1-40) was dissolved in 200 μL of DMSO, and after sealing, the solution was kept in a refrigerator at −20° C. for no more than one week for future use. Before use, the DMSO solution of the amyloid polypeptide was diluted with profuse phosphate buffer solution (PBS, 20 mM, pH=7.4) till the concentration of Aβ(1-40) reached 20 μM to obtain an Aβ(1-40) PBS solution. All the Aβ(1-40) PBS solutions for the experiments were prepared freshly.

2) Sample Preparation and Detection

Ligand-modified AuCs and gold nanoparticles were added to 20 μM Aβ(1-40) PBS respectively to form samples of AuCs modified with different ligands at different concentrations and different particle sizes, and samples of gold nanoparticles modified with different ligands correspondingly. The samples were incubated continuously in a 96-well plate at 37° C. by ThT fluorescent labeling method, and monitored the fluorescence intensity by microplate reader once every 10 minutes. The kinetic process of Aβ(1-40) aggregation was characterized through the change of fluorescence intensity of ThT.

Three sizes of L-NIBC-modified AuCs with particle sizes of 2.6 nm, 1.8 nm and 1.1 nm respectively prepared in Embodiment 2 were used as experiment groups. Four sizes of L-NIBC-modified gold nanoparticles with particle sizes of 18.2 nm, 10.1 nm, 6.0 nm and 3.6 nm respectively, and L-NIBC molecules uncombined with AuCs or gold nanoparticles were used as control groups. Every size of AuCs or gold nanoparticles were in six concentrations respectively, which were: 0 ppm (not containing AuCs, gold nanoparticles or L-NIBC, as blank control), 0.1 ppm, 1.0 ppm, 5.0 ppm, 10.0 ppm and 20.0 ppm respectively. L-NIBC molecules in two concentrations were used, which were: 1.0 ppm and 10.0 ppm respectively.

Figure 5:
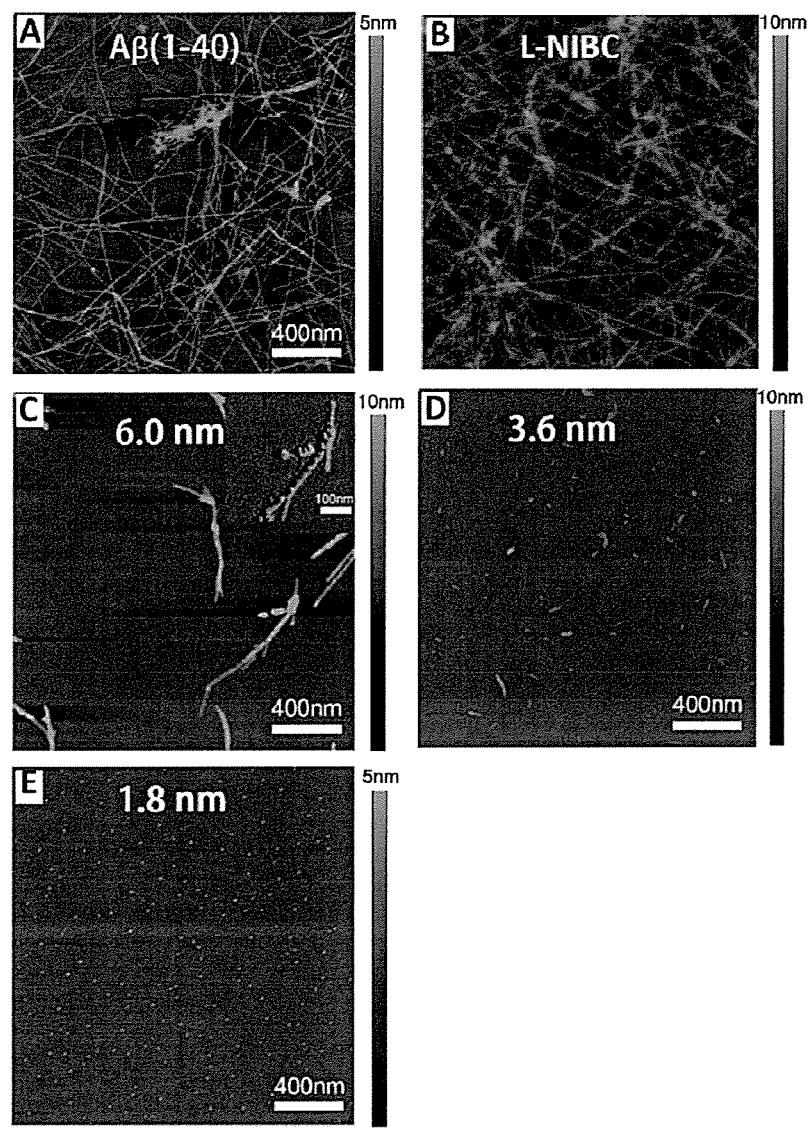
FIG. 5 shows AFM topographies after Aβ (1-40) and ligand L-NIBC-modified gold nanoparticles or AuCs are co-incubated for 48 h.
Figure 6:
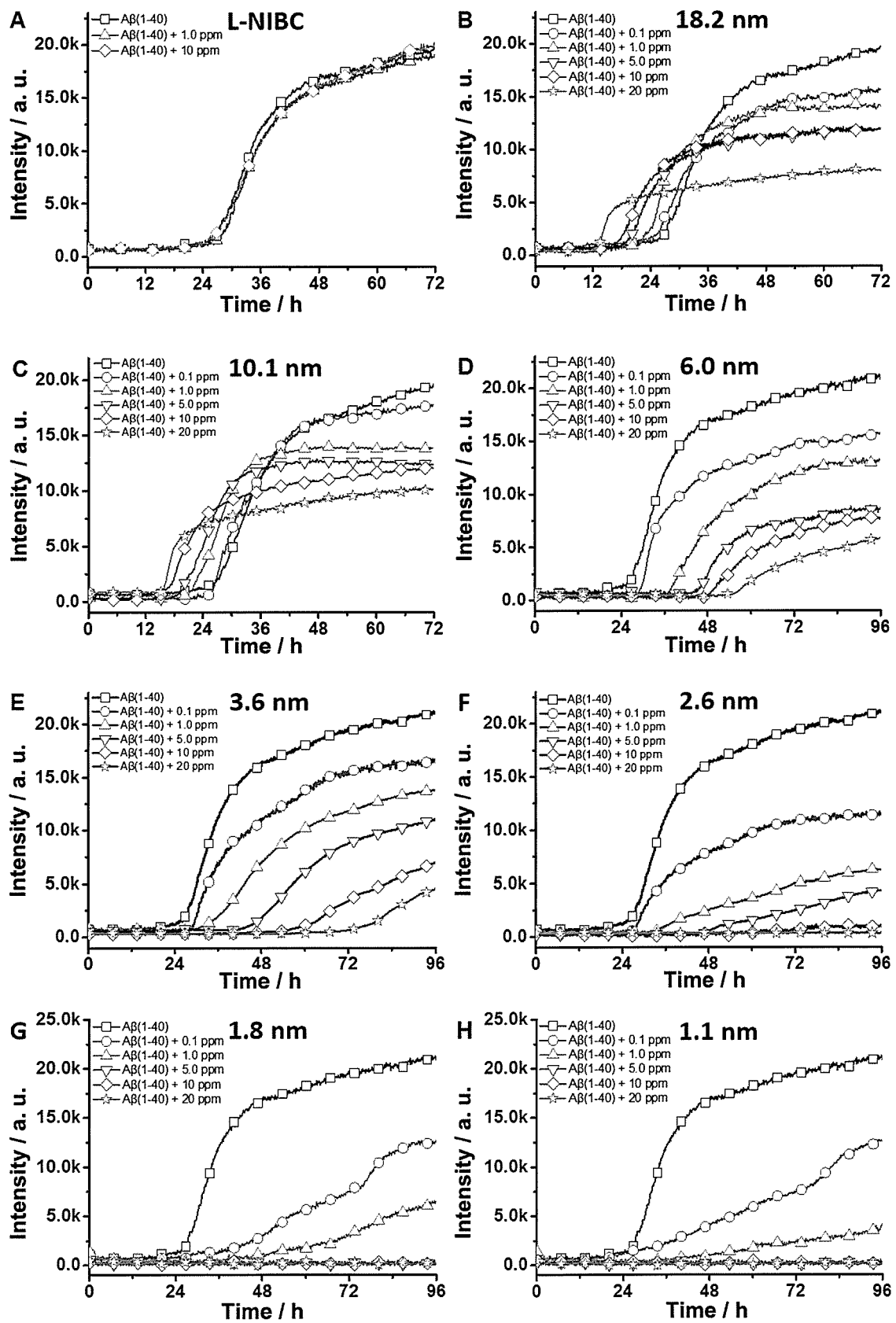
FIG. 6 shows kinetic curves of Aβ fibrosis with ligand L-NIBC-modified gold nanoparticles or AuCs of different particle sizes and different concentrations.
Figure 7:
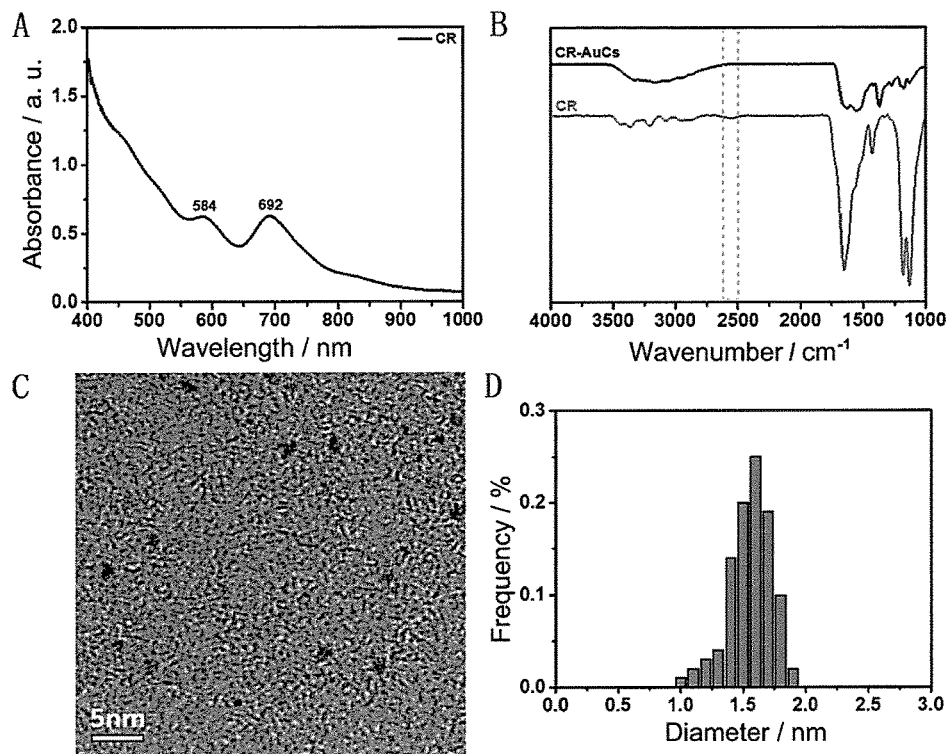
FIG. 7 shows UV, infrared, TEM and particle size distribution diagrams of ligand CR-modified AuCs (CR-AuCs).
Figure 8:
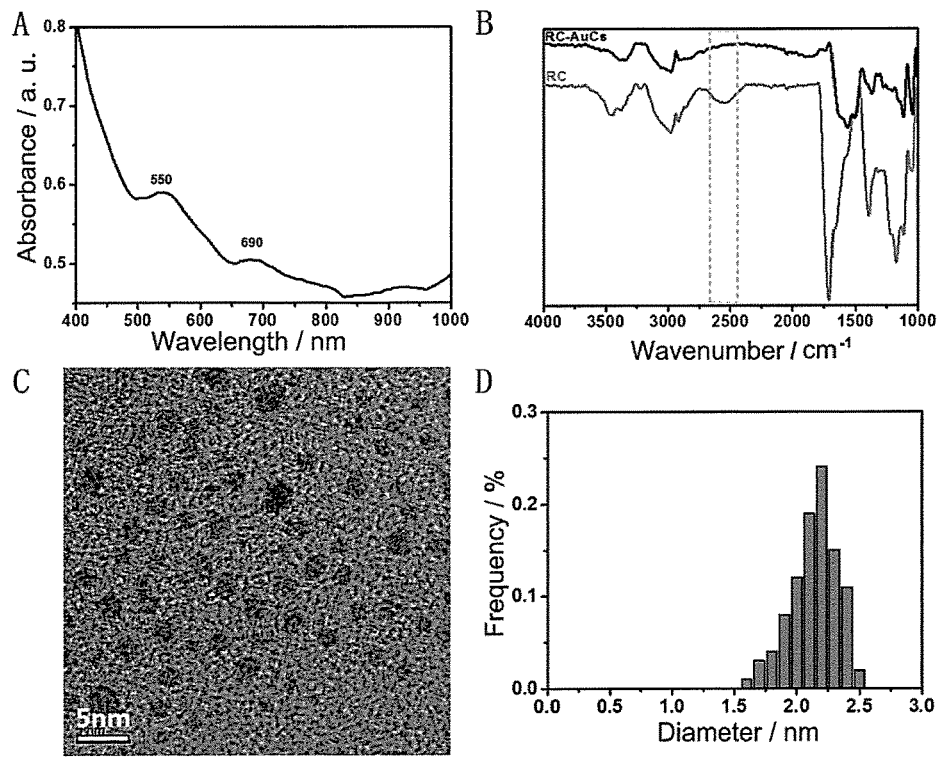
FIG. 8 shows UV, infrared, TEM and particle size distribution diagrams of ligand RC-modified AuCs (RC-AuCs).
Figure 9:
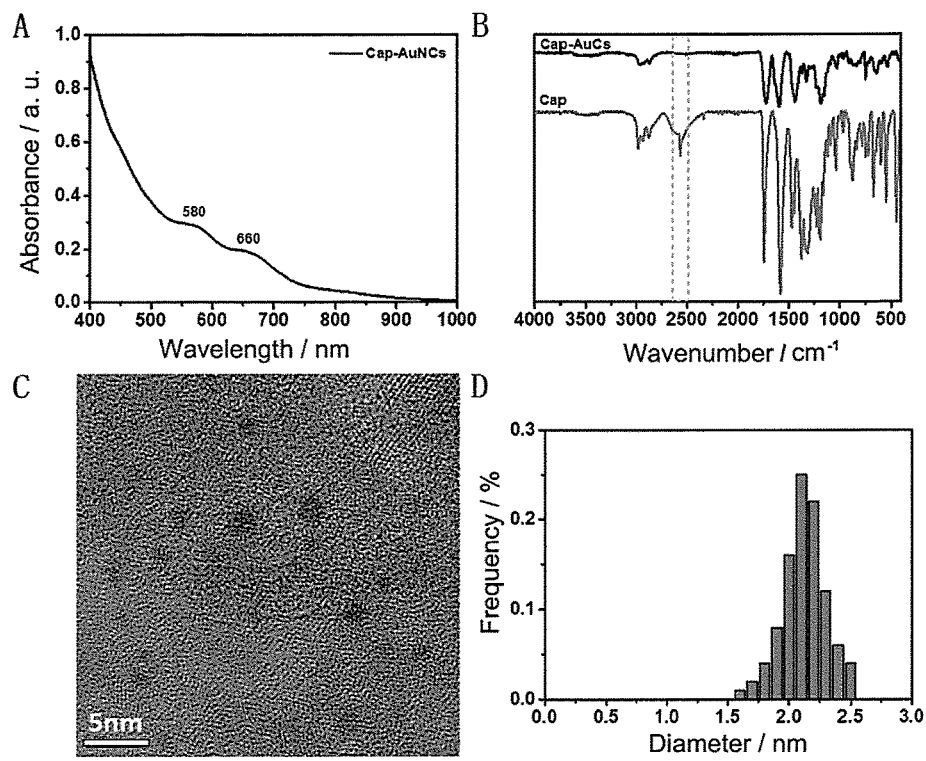
FIG. 9 shows UV, infrared, TEM and particle size distribution diagrams of ligand 1-[(2S)-2-methyl-3-thiol-1-oxo-propyl]-L-proline (i.e., Cap)-modified AuCs (Cap-AuCs).
Figure 10:
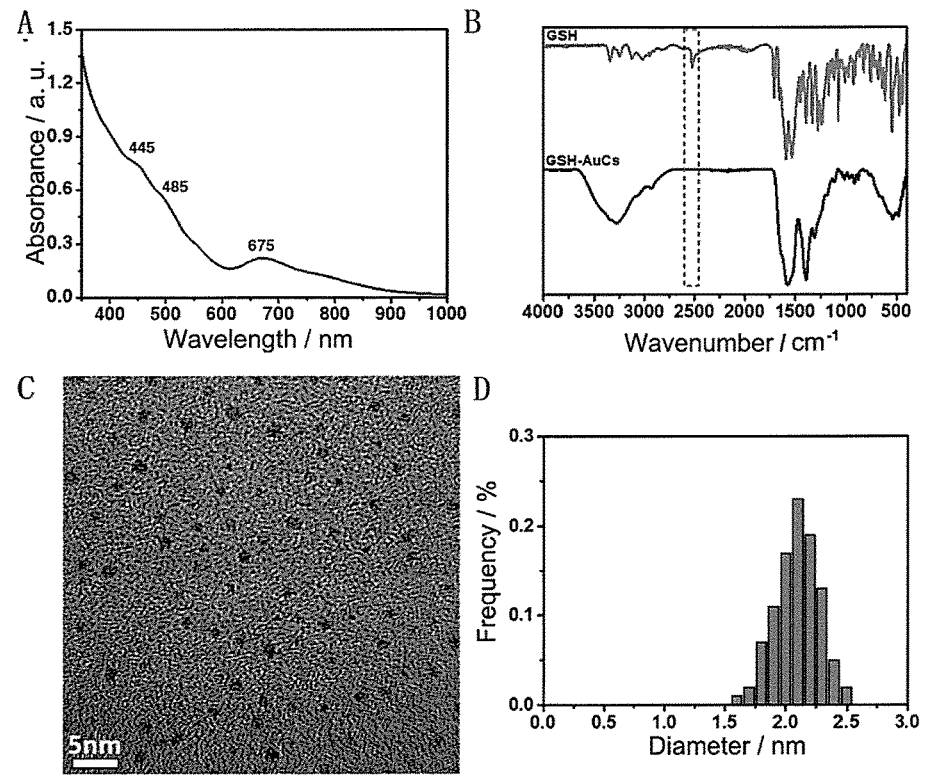
FIG. 10 shows UV, infrared, TEM and particle size distribution diagrams of ligand GSH-modified AuCs (GSH-AuCs).
Figure 11:
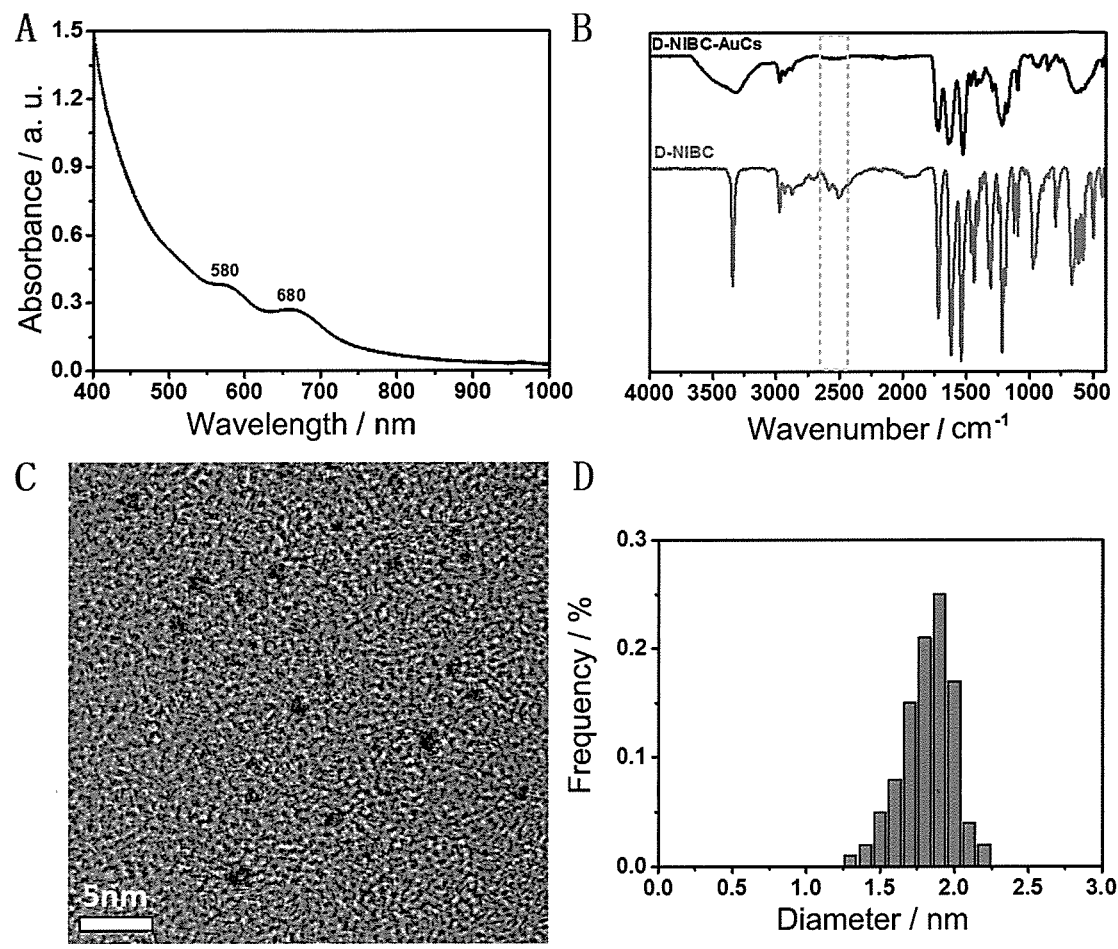
FIG. 11 shows UV, infrared, TEM and particle size distribution diagrams of ligand D-NIBC-modified AuCs (D-NIBC-AuCs).

The results are shown in FIG. 5 and FIG. 6.

FIG. 5 shows AFM topographies of Aβ(1-40) after coincubating with each experiment group and control group for 48 h. Panel A is the AFM topography after Aβ(1-40) was incubated alone for 48 h. Panel B is an AFM topography after Aβ(1-40) was coincubated with L-NIBC for 48 h. Panel C and panel D are AFM topographies after Aβ(1-40) was coincubated with gold nanoparticles with an average particle size of 6.0 nm and 3.6 nm respectively (modified with L-NIBC) for 48 h. And panel E is an AFM topography after Aβ(1-40) was coincubated with AuCs in an average particle size of 1.8 nm (modified with L-NIBC) for 48 h.

In FIG. 6, the amyloidosis kinetics curve of Aβ(1-40) in different concentrations of L-NIBC is shown in panel A. The amyloidosis kinetics curves of Aβ(1-40) in different concentrations of gold nanoparticles with sizes of 18.2 nm, 10.1 nm, 6.0 nm and 3.6 nm respectively are shown in panel B-E. The amyloidosis kinetics curves of Aβ(1-40) in different concentrations of AuCs with sizes of 2.6 nm, 1.8 nm and 1.1 nm respectively are shown in panel F-H. The amyloidosis kinetics curves of Aβ in panels A-H are curves when Aβ(1-40) was coincubated gold nanoparticles or AuCs in different concentrations, □ represented 0 ppm (i.e., no gold nanoparticles and AuCs), ○ represented 0.1 ppm, Δ represented 1 ppm, ? represented 5 ppm, ? represented 10 ppm, * represented 20 ppm.

It could be seen from FIG. 5 that as control, Aβ fibers was filled in panel A; the same as panel B; though fibers reduced to some extent, long fibers could still be seen in panel C; though there were no long fibers, many Aβ short fibers still existed in panel D. It was indicated that L-NIBC had no obvious effect on the formation of Aβ(1-40) fibers. The addition of L-NIBC-modified small-size gold nanoparticles could delay the amyloidosis process of Aβ(1-40), but not inhibit completely because short fibers would continue to grow into long fibers after more time. It has neither long fibers nor short fibers in panel E of FIG. 5, what was suggested that L-NIBC-modified AuCs could inhibit the amyloidosis process of Aβ(1-40) completely.

FIG. 5 is a qualitative experiment, but FIG. 6 is a quantitative experiment. The result of FIG. 6 indicates that the addition of L-NIBC had no obvious effect on Aβ(1-40) amyloidosis kinetics (panel A of FIG. 6); for gold nanoparticles, when the particle diameter was greater than or equal to 10.1 nm, the addition of L-NIBC-modified gold nanoparticles pushed forward both the growth stage and platform stage of Aβ aggregation kinetics (when the concentration of gold nanoparticles was 20 ppm, the growth stage of Aβ aggregation kinetics was pushed forward to $12^{th}$ h, and the platform stage was pushed forward to $16^{th}$ h), suggesting that L-NIBC-modified gold nanoparticles could accelerate Aβ aggregation (panels B and C of FIG. 6); when the diameter of gold nanoparticles was smaller than or equal to 6.0 nm (panel D and E of FIG. 6), the starting time of Aβ aggregation could be delayed (when the concentration of L-NIBC-modified gold nanoparticles was 20 ppm, the growth stage of Aβ aggregation kinetics was delayed to $54^{th}$ h), suggesting that gold nanoparticles had an inhibitory effect on Aβ aggregation. However, FIG. 6 indicates that even if the concentration was very high (20.0 ppm), the addition of L-NIBC-modified gold nanoparticles was unable to inhibit completely (i.e., no growth stage appeared, and the fluorescent curve was completely flat). On the other hand, after addition of L-NIBC-modified gold nanoparticles, since the fluorescence emission peak of ThT locates at 515 nm, while the plasmon resonance absorption peak of L-NIBC-modified gold nanoparticles locates near 520 nm, the decrease of ThT fluorescent intensity observed here should be the partial quenching of the plasmon resonance effect of the gold nanoparticles to ThT fluorescence, but should not be attributed to the inhibitory effect of L-NIBC-modified gold nanoparticles on Aβ(1-40) aggregation.

Panels F-H of FIG. 6 indicate that all the L-NIBC-modified AuCs could significantly inhibit Aβ aggregation (the starting time of the growth stage was postponed. When the concentration of L-NIBC-modified AuCs was 5 ppm, the starting time of the growth stage in aggregation kinetics of 20 μM Aβ could be delayed to later than 50 h). When the concentration of L-NIBC-modified AuCs was 10 ppm or above, Aβ aggregation could be completely inhibited (growth stage did not appear, and the fluorescent curve was completely flat). The minimum concentration of L-NIBC-modified AuCs needed for complete inhibition is relevant to the ligand type and the diameter of AuCs. The minimum concentrations of L-NIBC-modified AuCs with sizes of 1.1 nm, 1.8 nm and 2.6 nm were 5.0 ppm, 5.0 ppm and 10.0 ppm respectively. Besides, as L-NIBC-modified AuCs do not have plasmon resonance effect, they do not have quenching effect on ThT fluorescence. Therefore, the decrease in fluorescence intensity observed here was entirely due to the inhibitory effect of L-NIBC-modified AuCs on Aβ(1-40) aggregation. The quantitative results of FIG. 6 are in good agreement with the qualitative results of FIG. 5.

This experiment indicates that: when the size of L-NIBC-modified gold nanoparticles is smaller than or equal to 6.0 nm, they have certain inhibitory effect on Aβ aggregation and fibrosis, but limitedly; L-NIBC-modified AuCs has the function of completely inhibiting Aβ aggregation and fibrosis. As L-NIBC molecules per se cannot influence the aggregation and fibrosis of Aβ (in view of panel B of FIG. 5 and panel A of FIG. 6), this function is from AuCs, but not L-NIBC ligand.

This experiment result provided forceful support for the research and development of using AuCs to form medication against diseases related to Aβ aggregation and fibrosis, which laid a foundation for the formation of medication for Aβ aggregation and fibrosis-related diseases (such as: glaucoma). L-NIBC-modified AuCs can be classified as substances containing AuCs as defined in the present invention.

Figure 12:
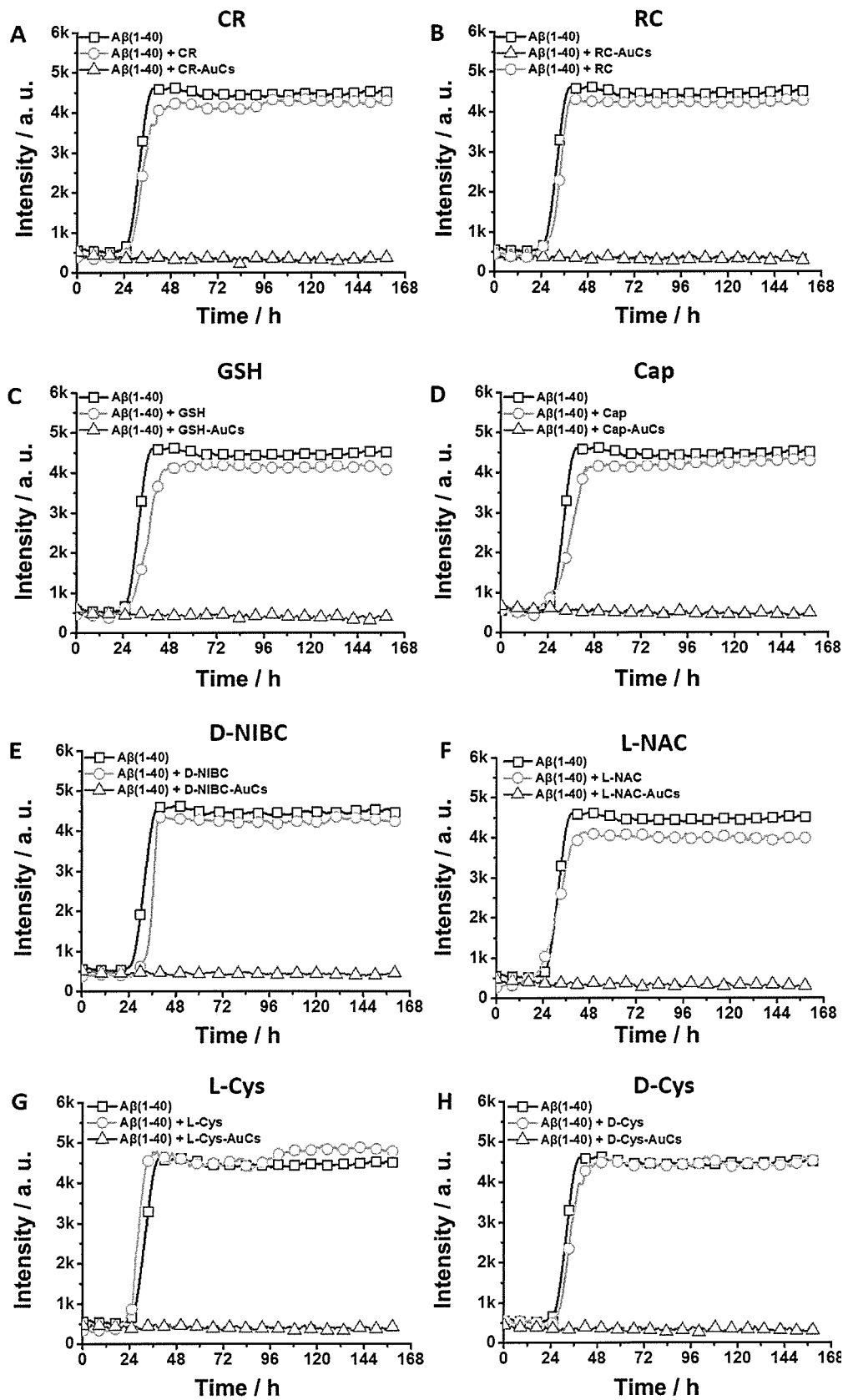
FIG. 12 shows curves of the inhibitory effect of AuCs modified with different ligands on the aggregation and fibrosis of Aβ (1-40).

This embodiment also validates the functions of AuCs modified with other ligands listed in Table 1. For example, panels A-H of FIG. 12 show the inhibitory effect of AuCs modified with CR, N-acetyl-L-cysteine (L-NAC), GSH, 1-[(2S)-2-methyl-3-thiol-1-oxopropyl]-L-proline (Cap), D-NIBC, RC or L-cysteine and D-cysteine (the dose is 10 ppm) on Aβ(1-40) aggregation and fibrosis. A similar phenomenon was observed for AuCs modified with different ligands, and the same conclusion can be made: These ligands per se cannot influence Aβ aggregation and fibrosis, the ligand-modified gold nanoparticles with a size of greater than 3 nm have a limited inhibitory effect on Aβ aggregation and fibrosis, and larger gold nanoparticles even promote Aβ aggregation and fibrosis; but ligand-modified AuCs have excellent inhibitory effect on Aβ aggregation and fibrosis, and when the concentration is above 5-10 ppm, effect of complete inhibition can be achieved, while the minimum concentration needed for complete inhibition varies slightly with ligand and particle size of AuCs. Likewise, these ligand-modified AuCs are classified into AuCs-containing substances defined in the present invention.

Since AuCs cannot exist stably in a solution without ligands, AuCs are modified with ligands in this experiment. But the experiment results have indicated that AuCs per se influence Aβ aggregation and fibrosis as functional ingredients. Therefore, other changes made based on the foregoing functions of the AuCs contributed in the present invention, such as no ligands, changing of ligands, active or inactive ligands, and combined use of AuCs and other vectors or medications, are all made based on the present invention.

Embodiment 4: $H_2O_2$-Induced RGC-5 Cell Oxidative Stress Injury Model Experiment The cell viability was used as an index in the experiment of this embodiment. The test result of CCK-8 method reflected the effects of ligand-modified AuCs on the $H_2O_2$-induced cytotoxicity, and showed that ligand-modified AuCs had a neuroprotective effect on the oxidative stress injury mechanism of ganglion cells.

Experiment 1:

RGC-5 cells in logarithmic growth phase were diluted with complete medium (MEM+10% FBS+1% penicillin—streptomycin) to get a cell suspension in a density of $5 \times 10^4$/mL. The suspension was inoculated 100 μL per well into a 96-well plate, and cultivated in an incubator with 5% $CO_2$ at 37° C. One of administration ways in an experiment group is: The original culture medium was removed when the cells attached to the wells, and 50 μL test substances (the test substances were: three kinds of L-NIBC-modified AuCs in particle sizes of 2.6 nm, 1.8 nm or 1.1 nm, or four kinds of L-NIBC-modified gold nanoparticles in particle sizes of 18.2 nm, 10.1 nm, 6.0 nm or 3.6 nm, or L-NIBC molecules not bonded with AuCs or gold nanoparticles as reference) solutions at different concentrations prepared by maintenance medium (DMEM medium+2% FBS+1% penicillin-streptomycin) were added to different wells to make the final concentration be 0.01, 0.05, 0.1, 0.5, 1, 5 and 10 ppm respectively, then 50 μL of $H_2O_2$ (the final concentration was 100 μM) was added to the administration group and model group after 2 hours' pretreatment. The cells were incubated for 24 h, then 10% CCK-8 was added to each well and incubated for 4 h. The absorbance value of each well at 450 nm wave length was measured to evaluate the pre-protective effect of AuCs on $H_2O_2$ injury. The other administration ways in an experiment group is: The original culture medium was removed when the cells attached to the wells, 50 μL of $H_2O_2$ solution prepared by maintenance medium was added to different wells (the final concentration was 100 μM), and incubated for 4 h, 8 h, 12 h and 24 h respectively, and then 50 μL of test substance solution prepared by maintenance medium at different concentrations was added to each group of wells at different incubation time to make the final concentration be 0.01, 0.05, 0.1, 0.5, 1, 5 and 10 ppm, then was incubated for 24 h respectively. Then 10% CCK-8 was added to each well, and incubated for 4 h. The absorbance value of each well at 450 nm wave length was measured to evaluate the curative effect of AuCs on $H_2O_2$ injury. In the above experiment, a blank control group without cells, a control group without treating cells and an injury control group with cells being treated by 100 μM $H_2O_2$ were set.

The results showed that the ligand-modified AuCs provided in the present invention could significantly increase the cell viability of $H_2O_2$-injured in RGC cell model, which indicated that they could resist RGC apoptosis triggered by oxidative stress. In comparison, the gold nanoparticles modified with the same ligand but in a larger size did not have a good or obvious effect on RGC apoptosis triggered by oxidative stress, and L-NIBC did not have an obvious effect on RGC apoptosis triggered by oxidative stress. AuCs modified with different ligands had a similar effect, while the corresponding ligands per se did not have an obvious effect, which indicated that this effect was originated from AuCs, rather than the ligand.

Experiment 2:

RGC-5 cells in logarithmic growth phase were diluted with complete medium (MEM+10% FBS+1% penicillin—streptomycin) to get a cell suspension in a density of $5\times10^4$/mL. The suspension was inoculated 100 μL per well into a 96-well plate, and cultivated in an incubator with 5% $CO_2$ at 37° C. The original culture medium was removed when the cells attached to the wells, and 50 μL solutions of AuCs or gold nanoparticles at different concentrations prepared by maintenance medium (DMEM medium +2% FBS+ 1% penicillin-streptomycin) were added to different wells to make the final concentration be 0.1, 1 and 10 ppm respectively, then 50 μL of $H_2O_2$ (the final concentration was 105 μM) was added to the administration group and model group after 2 hours' pretreatment. The cells were incubated for 24 h, then 10% CCK-8 was added to each well and incubated for 4 h. The absorbance value of each well at 450 nm wave length was measured to evaluate the pre-protective effect of AuCs on $H_2O_2$ injury. In the above experiment, a blank control group without any treatment, a model control group of cells treated with 105 μM $H_2O_2$, an AuCs control group of cells added with 100 ppm AuCs but without $H_2O_2$, and a ligand control group of cells added with 10 ppm of ligand and 105 μM of $H_2O_2$ but without AuCs or gold nanoparticles were set at the same time.

Figure 13:
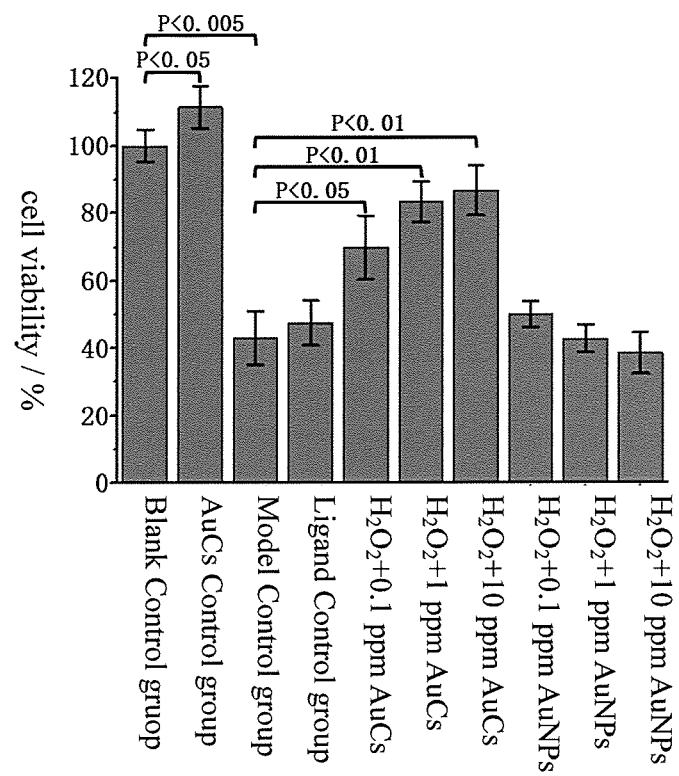
FIG. 13 shows the effect of ligand L-NIBC-modified AuCs or gold nanoparticles on the cell viability of $H_2O_2$-induced oxidative stress glaucoma in RGC-5 cell model.

The experiment results of L-NIBC-modified AuCs or gold nanoparticles for example were shown in FIG. 13. The results indicated that after 24 hours' cultivation, the cell viability of the AuCs control group added with 100 ppm AuCs, but not treated with $H_2O_2$ increased to 111.5±6.2% relative to the blank control group (set to be 100%) (P<0.05), which suggested AuCs were nontoxic. The cell viability of the model control group added with 100 μM $H_2O_2$ but without AuCs or gold nanoparticles decreased to 43.0±7.8% (relative to the blank control group, P<0.005), and the cell viability of the ligand control group added with 10 ppm L-NIBC and 100 μM $H_2O_2$, but without AuCs or gold nanoparticles was 47.5±6.6% (relative to the blank control group, P<0.01; and the model control group, P>0.05), which suggested that ligand alone did not increase the cell viability of $H_2O_2$-injured cell model. While the cell viability of the administration group added with 0.1 ppm, 1 ppm and 10 ppm of AuCs increased to 69.8±9.5% (relative to the model control group, P<0.05), 83.3±6.1% (relative to the model control group, P<0.01) and 86.8±7.4% (relative to the model control group, P<0.01) respectively. On the other hand, the gold nanoparticles of corresponding ligand in an average size of 6.0 nm at three experimental concentrations had no obvious difference from the model control group in terms of cell viability (P>0.05).

The above results indicated that the ligand-modified AuCs provided in the present invention could significantly increase the cell viability in $H_2O_2$-injured RGC cell model, which suggested that they could resist RGC apoptosis triggered by oxidative stress, while L-NIBC did not have an obvious effect against RGC apoptosis triggered by oxidative stress, and this effect was from AuCs rather than ligand. The gold nanoparticles modified with the same ligand but in a larger size did not have an obvious effect against RGC apoptosis triggered by oxidative stress, which suggested that gold nanoparticles could not be used as drugs preventing and treating glaucoma.

The AuCs or gold nanoparticles modified with different ligands listed in Table 1 were adopted the same steps to carry out the experiment. The effects were similar, so they would not be described in details herein.

Embodiment 5: N-methyl-D-asparagic Acid (NMDA)-induced RGC-5 Cell Excitotoxity Model Experiment This embodiment used cell survival rate as an index. The test result of cck-8 method reflected the effect of ligand-modified AuCs against NMDA-induced cytotoxicity to show that AuCs had a neuroprotective effect on the neurotransmitter excitotoxic injury mechanism.

RGC-5 cells in logarithmic growth phase were diluted with complete medium to get a cell suspension in a density of $5\times10^4$/mL. The suspension was inoculated 100 μL per well into a 96-well plate, and cultivated in an incubator with 5% $CO_2$ at 37° C. One of administration ways in an experiment group is: The original culture medium was removed when the cells attached to the wells, and 50 μL test substances (the test substances were: three kinds of L-NIBC-modified AuCs in particle sizes of 2.6 nm, 1.8 nm or 1.1 nm, or four kinds of L-NIBC-modified gold nanoparticles in particle sizes of 18.2 nm, 10.1 nm, 6.0 nm or 3.6 nm, or L-NIBC molecules not bonded with AuCs or gold nanoparticles as reference) solutions at different concentrations prepared by maintenance medium were added to different wells to make the final concentration be 0.01, 0.05, 0.1, 0.5, 1, 5 and 10 ppm respectively, then 50 μL of NMDA (the final concentration was 250 μM) was added to the administration group and model group after 2 hours' pretreatment. The cells were incubated for 24 h, then 10% CCK-8 was added to each well and incubated for 4 h. The absorbance value of each well at 450 nm wave length was measured to evaluate the pre-protective effect of AuCs on NMDA injury. The other administration ways in an experiment group is: The original culture medium was removed when the cells attached to the wells, 50 μL of NMDA solution prepared by maintenance medium was added (the final concentration was 250 μM), and incubated for 4 h, 8 h, 12 h and 24 h respectively, and then 50 μL of test substance solution prepared by maintenance medium at different concentrations was added to make the final concentration be 0.01, 0.05, 0.1, 0.5, 1, 5 and 10 ppm, then was incubated for 24 h respectively. Then 10% CCK-8 was added to each well, and incubated for 4 h. The absorbance value of each well at 450 nm wave length was measured to evaluate the curative effect of AuCs on NMDA injury. In the above experiment, a blank control group without cells, a control group without treating cells and an injury control group with cells being treated by 250 μM NMDA were set.

The results showed that the ligand-modified AuCs provided in the present invention could significantly increase the cell viability of NMDA-induced excitotoxic injury in RGC cell model, which indicated that they could inhibit neurotransmitter mediated excitatory RGC apoptosis. In comparison, the gold nanoparticles modified with the same ligand but in a larger size did not have a good or obvious effect on neurotransmitter mediated excitatory RGC apoptosis, and L-NIBC did not have an obvious effect on neurotransmitter mediated excitatory RGC apoptosis. AuCs modified with different ligands had a similar effect, while the corresponding ligands per se did not have an obvious effect, which indicated that this effect was originated from AuCs, rather than the ligand.

Embodiment 6: Sodium Nitroprusside (SNP)-induced RGC-5 Apoptosis Model Experiment The cell viability was used as an index in the experiment of this embodiment. The test result of CCK-8 method reflected the effects of ligand-modified AuCs on the SNP-induced cytotoxicity and showed that ligand-modified AuCs had a neuroprotective effect on the RGC-5 apoptosis induced by SNP.

Experiment 1:

RGC-5 cells in logarithmic growth phase were diluted with complete medium to get a cell suspension in a density of $5 \times 10^4$/mL. The suspension was inoculated 100 µL per well into a 96-well plate, and cultivated in an incubator with 5% $CO_2$ at 37° C. One of administration ways in an experiment group is: The original culture medium was removed when the cells attached to the wells, and 50 µL test substances (the test substances were: three kinds of L-NIBC-modified AuCs in particle sizes of 2.6 nm, 1.8 nm or 1.1 nm, or four kinds of L-NIBC-modified gold nanoparticles in particle sizes of 18.2 nm, 10.1 nm, 6.0 nm or 3.6 nm, or L-NIBC molecules not bonded with AuCs or gold nanoparticles as reference) solutions at different concentrations prepared by maintenance medium were added to make the final concentration be 0.01, 0.05, 0.1, 0.5, 1, 5 and 10 ppm respectively, then 50 µL SNP solution (the final concentration was 750 µM) prepared by maintenance medium was added to the administration group and model group after 2 hours' pretreatment. The cells were incubated for 24 h, then 10% CCK-8 was added to each well and incubated for 4 h. The absorbance value of each well at 450 nm wave length was measured to evaluate the pre-protective effect of AuCs on SNP injury. The other administration ways in an experiment group is: The original culture medium was removed when the cells attached to the wells, 50 µL of SNP solution prepared by maintenance medium was added (the final concentration was 750 µM), and incubated for 4 h, 8 h, 12 h and 24 h respectively, and then 50 µL of test substance solution prepared by maintenance medium at different concentrations was added to make the final concentration be 0.01, 0.05, 0.1, 0.5, 1, 5 and 10 ppm, then was incubated for 24 h respectively. Then 10% CCK-8 was added to each well, and incubated for 4 h. The absorbance value of each well at 450 nm wave length was measured to evaluate the curative effect of AuCs on SNP injury. In the above experiment, a blank control group without cells, a control group without treating cells and an injury control group with cells being treated by 250 µM SNP were set.

The results showed that the ligand-modified AuCs provided in the present invention could significantly increase the cell viability of SNP-injured in RGC cell model, which indicated that they had a protective effect on RGC apoptosis induced by cerebral ischemia and hypoxia. In comparison, the gold nanoparticles modified with the same ligand but in a larger size did not have a good or obvious protective effect on RGC apoptosis induced by cerebral ischemia and hypoxia, and L-NIBC did not have an obvious protective effect on RGC apoptosis induced by cerebral ischemia and hypoxia. AuCs modified with different ligands had a similar effect, while the corresponding ligands per se did not have an obvious effect, which indicated that this effect was originated from AuCs, rather than the ligand.

Experiment 2:

RGC-5 cells in logarithmic growth phase were diluted with complete medium to get a cell suspension in a density of $5 \times 10^4$/mL. The suspension was inoculated 100 µL per well into a 96-well plate, and cultivated in an incubator with 5% $CO_2$ at 37° C. One of administration ways in an experiment group is: The original culture medium was removed when the cells attached to the wells, and 50 µL solutions of AuCs or gold nanoparticles at different concentrations prepared by maintenance medium were added to make the final concentration be 0.1, 1 and 10 ppm respectively, then 50 µL SNP solution (the final concentration was 700 µM) prepared by maintenance medium was added to the administration group and model group after 2 hours' pretreatment. The cells were incubated for 24 h, then 10% CCK-8 was added to each well and incubated for 4 h. The absorbance value of each well at 450 nm wave length was measured to evaluate the pre-protective effect of AuCs on SNP injury. In the above experiment, a blank control group without any treatment, a model control group of cells treated with 700 µM SNP, an AuCs control group of cells added with 100 ppm AuCs but without SNP, and a ligand control group of cells added with 10 ppm of ligand and 700 µM of SNP but without AuCs or gold nanoparticles were set at the same time.

Figure 14:
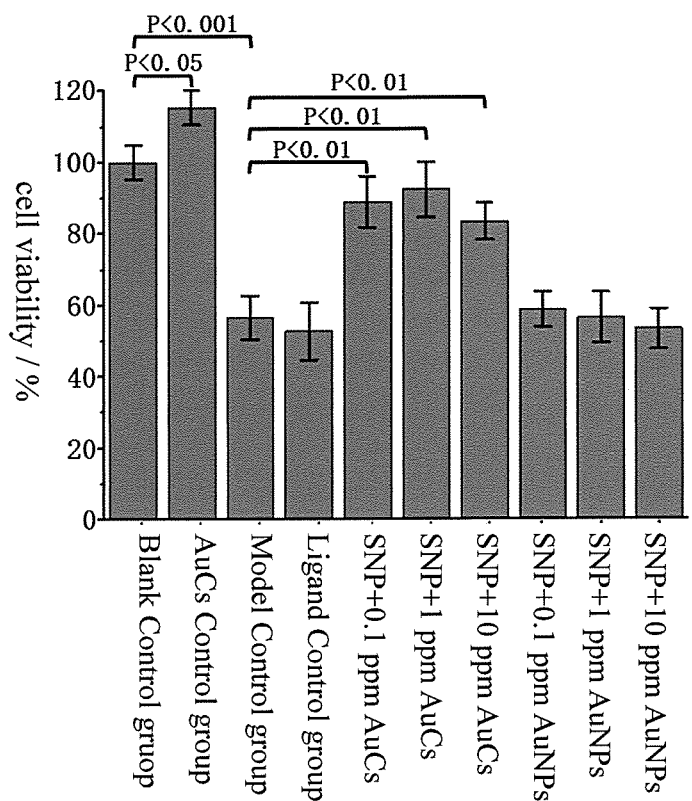
FIG. 14 shows the effect of ligand L-NIBC-modified AuCs or gold nanoparticles on the cell viability of sodium nitroprusside-induced apoptosis glaucoma in RGC-5 cell model.

The experiment results of L-NIBC-modified AuCs or gold nanoparticles for example were shown in FIG. 14. The results indicated that after 24 hours' cultivation, the cell viability of the AuCs control group added with 100 ppm AuCs, but not treated with SNP increased to 115.4±4.8% relative to the blank control group (set to be 100%) (P<0.05), which suggested AuCs were nontoxic. The cell viability of the model control group decreased to 56.7±6.0% (relative to the blank control group, P<0.001), and the cell viability of the ligand control group was 52.8±8.0% (relative to the blank control group, P<0.01; and the model control group, P>0.05), which suggested that ligand alone did not increase the cell viability in SNP-injured cell model. While the cell viability of the administration group added with 0.1 ppm, 1 ppm and 10 ppm of AuCs increased to 89.0±7.2% (relative to the model control group, P<0.01), 92.5±7.7% (relative to the model control group, P<0.01) and 83.5±5.2% (relative to the model control group, P<0.01) respectively. On the other hand, the gold nanoparticles of corresponding ligand in an average size of 6.0 nm at three experimental concentrations had no obvious difference from the model control group in terms of cell viability (P>0.05).

The above results indicated that the ligand-modified AuCs provided in the present invention could significantly increase the cell viability in SNP-injured RGC cell model, which suggested that they could resist SNP-induced RGC apoptosis, while L-NIBC did not have an obvious effect against SNP-induced RGC apoptosis, and this effect was from AuCs rather than ligand. The gold nanoparticles modified with the same ligand but in a larger size did not have an obvious effect against SNP-induced RGC apoptosis, which suggested that gold nanoparticles could not be used as drugs preventing and treating glaucoma.

The AuCs or gold nanoparticles modified with different ligands listed in Table 1 were adopted the same steps to carry out the experiment. The effects were similar, so they would not be described in details herein.

Embodiment 7: Optic Nerve Crush Injury Rat Model Experiment

The optic nerve crush injury rat model is a widely-used animal model for glaucoma without a high intraocular pressure. The model is an incomplete injury model that is prepared by clamping rat's optic nerve with reverse forceps under a constant pressure. It maintains the integrity of the epineurium of optic nerve, is simple to operate, has good reproducibility, and is close to the clinical characteristics of glaucoma. It is a mature animal model for the research of glaucoma-related optic nerve damage and retinal function. In particular, this model is widely used in the pathological process of RGC death and in the research of drugs to inhibit or slow down optic nerve damage and RGC apoptosis.

Experiment 1:

1) Preparation of Rat Optic Nerve Clamping Injury Model

108 SPF adult male Brown Norway rats, after one-week adaptive feeding, were anesthetized with 5% chloral hydrate by intraperitoneal injection. The skin around the right eyes of rats was routinely disinfected. Under the binocular operating microscope, the lateral canthus and the conjunctiva were cut open, the Hada gland and lacrimal gland tissue were pushed open and separated along the scleral wall to the external rectus muscle. The optic nerve was separated and exposed. The optic nerve was clamped with a non-invasive vascular clamp at 1 mm posterior to the eyeball for 10 s to cause injury of the optic nerve. Blood vessels should be avoided during the clamping process. After the end of the clamping, the broken end of the external rectus muscle and the layers of tissue were sutured to restore the conjunctival sac. After the operation, the condition of the fundus retinal vessels was observed, tobradex eyedrops were applied and the eyelid was sutured. On the first day after the operation, whether the rat optic nerve clamping model had been successfully prepared was observed. It was considered as a successful model if no complications (such as retinal ischemia and preretinal vitreous hemorrhage) were observed. The unsuccessful models would be removed from the experiment. The left eyes of all rats were not treated as control.

2) Animal experiment: 108 optic nerve clamping injury model rats were divided into three groups in random according to dosing time, namely: Day 7, Day 14 and Day 21 sampling groups, n=36 rats/group. Each group was further randomly divided into 3 sub-groups, including high dose group (concentration of AuCs: 5 g/L), low dose group (concentration of AuCs: 1 g/L) and control group (normal saline), n=12 rats/group. From the day of model preparation, 20 μl/eye of the test compound solution was dropwise added to the right eyes of rats in the high dose group and the low dose group. From the day of the model successfully preparation, 10 μl/eye of normal saline was dropwise added to the right eyes of rats in the control group. 10 μl/eye of normal saline was dropwise added to the left eyes of rats (including the control group, high dose group and low dose group) as control. The dropwise adding frequency and time were 3 times/day (7.00 am, 3.00 pm and 11.00 pm), for 7 days, 14 days and 21 days respectively.

3) Detection Indicators and Detection Methods

Ocular fundus photos: Photos of the ocular fundus of every rat were taken Jul. 14, 2021 days before and after administration. After general anesthesia of the rats with 5% chloral hydrate by intraperitoneal injection, rat whiskers were cut off, mydriasis was performed to rats by compound topiramine eye drops, lens direction was adjusted with rat eyes exposed till the target blood vessels of retina were clearly visible on the screen, and color photos of ocular fundus were taken finally. Note: In the whole process, the cornea was moistened with hypromellose eye drops.

VEP (Visual Evoked Potential) detection: The VEP of two eyes of every rat was detected Jul. 14, 2021 days before and after the administration in reference to international clinical visual electrophysiology standard. After anesthesia of the animals with 5% chloral hydrate by intraperitoneal injection, mydriasis was performed to rats by compound topiramine eye drops. In order to reduce the interference resistance, hair on the body surface corresponding to the anterior fontanelle and visual cortex of the rats was removed. The rats were kept in a dark room and adapted to the environment for 30 min. Full field flash stimulator was adopted (stimulus frequency 1.0 Hz; frequency bandwidth 0.1 ~75 Hz). The analysis time was 250 ms, the sampling frequency was 2.7 Hz and it was overlapped for 100 times; measurement was conducted at least 3 times in a row. The skin recording electrode was 7 mm disc-shaped silver chloride, the working electrode was placed on the surface of the cornea, the reference electrode was placed on the ipsilateral crotch, and the ground electrode was placed in the subcutaneous tissue of the tail. When one eye was checked, the other eye was covered completely with an opaque black eye mask. The ab wave calibration method was adopted in the description of the VEP. In order to exclude other variation interferences of latency and amplitude, L5b and amplitude A5 consistent with the clinical practice were used as observation indicators. Each time 3 stable waveforms were observed and recorded, and the average values of L5b and A5 were used as observation values.

Conventional hematoxylin and eosin staining (HE staining): 6 rats were selected in random from each group and their eyeballs and the orbital optic nerves were completely removed after anesthesia with 5% chloral hydrate by intraperitoneal injection. They were rinsed with phosphate buffer saline (PBS) and the cornea, lens and vitreous were removed under an operating microscope. Eyecup and optic nerve were immersed in 4% paraformaldehyde buffer to fix them for 24 h. The tissue was taken out, rinsed with PBS for three times, and dehydrated with ethanol by gradient (50% ethanol for 90 min, 70% ethanol for 90 min, 85% ethanol for 90 min, 95% ethanol for 60 min, 100% ethanol for 60 min). It was soaked in 1:1 mixture of xylene and ethanol for 1 h, and then soaked in pure xylene for 1 h. Dipping paraffin, embedding and sectioning: The hyalinized tissue was immersed in 1:1 mixture of paraffin and xylene for 90 min, then placed in paraffin for 120 min, and cooled at once. Then, the eyecup specimens at 5 μm was sliced in a row, and baked at 60° C. for future use. The slides were immersed in xylene for 5 min and the operation was repeated for 3 times. The slides were immersed in ethanol by gradient in turn (100%, 90% and 70%) each for 5 min, and the sections were finally washed with tap water for 5 min. The slides were stained in hematoxylin stain for 5 min. The excess stain on the slides was washed off with water before the 10 s separation of the color with 75% HCl ethanol solution, and the slides were washed with tap water until the micronucleus and nuclear chromatin were clearly detected under a microscope. It was stained with 0.5% eosin solution for 5 min and dehydrated with 70%, 85%, 95% and 100% ethanol in turn for 2 min. It was hyalinized with xylene twice for 1 min each time. The excess xylene around the sections was wiped off (it was noted that they mustn't be in dry), a proper amount of neutral gum was quickly dropwise added, the slides were covered prior to retinal morphology and RGC changes were observed under an optical microscope and sample pictures.

Whole retinal patch, Brn3a immunofluorescence staining and computer image analysis of RGCs: 6 rats were selected in random from each group, their eyeballs were completely removed after anesthesia with 5% chloral hydrate by intraperitoneal injection and rinsed with PBS. The eyeballs were immersed in 4% paraformaldehyde buffer to fix them at room temperature for 30 min. Then the cornea, iris, and lens under an operating microscope were removed, and the remaining eyecup tissue was re-immersed in 4% paraformaldehyde buffer to fix them at room temperature for 30 min. 4 radial incisions were cut in the sclera to flat out the retina. The retina were gently peeled, rinsed with PBS once; then the vitreous was placed upward, and the residual glass was carefully removed with a brush tip, and retinal patch was prepared and dried at 4° C. overnight. The retinal patch was rinsed with PBS for 5 min for 3 times in total, and the whole retina was blocked with 0.5% Triton-X100 (prepared with PBS) blocking solution was confined at room temperature for 15 min. The excess blocking solution was rinsed with PBS for 5 min for 3 times in total, and then incubated with diluent containing Brn3a primary antibody (2% bovine serum albumin and 2% Triton-X100 were dissolved in PBS. The dilution factor of the antibody was 1:100) at 4° C. overnight. It was rinsed with PBS for 5 min for 3 times in total. The secondary antibody prepared with diluent (Cy3-labeled donkey anti-goat secondary antibody, dilution factor 1:200) was added and incubated at room temperature for 2 h. Finally, it was rinsed with PBS for 10 min for 3 times in total, blocked, then placed under a fluorescence microscope, and observed and photographed. Camera and Adobe Photoshop software were used to collect pictures from the test retinal patch with optic papillae as the center. Scion image analysis software (Scion Corp., Frederick, MD) was used to count the total number of Brn3a-positive retinal cells in the visual field (7,200 square microns, 40× magnification). RGCs were counted from 4-6 different regions with an equal distance from the optic papillae under the microscope. The average value was calculated to represent the comparison parameter of retinal labeled cell count. SPSS 21.0 statistics software (Chicago, IL) was adopted to conduct statistical analysis of data. The experimental data was expressed with the mean±standard deviation of the experiment (mean±SEM). Data was analyzed by variance, and the statistical analysis between groups was inspected by One-Way Anova. $P<0.05$ meant the difference was statistically significant.

The results showed that the ligand-modified AuCs provided in the present invention could narrow the visual field defect of the right eyes of the model rats in the administration group, reduce the RGCs apoptosis, improve the structure and arrangement of retinal cells, and play a significant role in relieving the right eye dysfunction of model rats, which indicated that AuCs could be used to prepare drugs to prevent and treat glaucoma.

Experiment 2:

1) Preparation of Optic Nerve Crush Injury Rat Model

SPF adult male Sprague Dawley (SD) rats, after adaption for one week, were anesthetized with ketamine (50 mg/kg) and xylazine (10 mg/kg) by intraperitoneal injection. The hair and skin around rat eyes were disinfected with a povidone iodine solution at a 1:10 dilution factor, and the conjunctival sac was washed with normal saline. The conjunctiva was cut open from the location about 2 mm above the lateral canthus to avoid expanded vessels, and blunt dissection was conducted backwards along the lateral rectus direction, and the bulbar conjunctiva was lifted, and the eyeball was slightly pulled forward to expose optic nerve. Forceps hamostatic was then used to clamp the optic nerve about 2 mm behind the eyeball for 30 s, the eyeball was carefully returned to the original place and ophthalmic antibiotic gel was applied to the operative conjunctival sac. The animals were put back to the cage and observed till coming round. Analgesic was given 1-3 days after the model was prepared. After the operation, whether the optic nerve crush rat model had been successfully prepared was observed. It was considered as a successful model if no complications (such as retinal ischemia and preretinal vitreous hemorrhage) were observed. The unsuccessful models would be removed from the experiment. The left eyes of all rats were not treated as control.

2) Animal experiment: The computer-generated random method was adopted to divide 60 SPF adult SD rats into 5 groups (n=12 rats/group). One of the groups of animals was not treated at all as normal control group. The right eyes of other groups of animals were used to prepare rat optic nerve crush model by clamping method. They were negative control group, low dose group, medium dose group and high dose group. The day of model preparation was recorded as the first day. 0.1 g/L, 0.2 g/L or 0.5 g/L L-NIBC-modified AuCs in normal saline solution were dropwise added to the right eyes of rats in the low dose, medium dose and high dose groups respectively three times a day with 10 µL/eye since the day of model preparation (the dosing interval was 5±0.5 h). Normal saline was dropwise added to the right eyes of the rats in the control group 3 times a day with 10 µL/eye since the day of model preparation as control. fVEP (flash visual evoked potentials) of the rats in each group were measured on Day 7 and Day 14 respectively. On Day 15, all animals were sacrificed. Their right eyes were taken out and properly treated, and undergone HE staining and immunofluorescence staining (n=6/group).

3) Detection Indicators and Detection Methods

Flash visual evoked potentials (fVEP): Roland Consult Electrophysiological Diagnostic Systems (RETIport VEP-ERG-AEP Version 6.16.3.4, Germany) were adopted to conduct fVEP check of all animals before the experiment, and then fVEP check of the right eyes of the animals were conducted in each group on Day 7 and Day 14. Main steps: Before examination, the animals were allowed to be adapted to darkness for at least 12 h. Mydriasis was performed to the animals with 1.0% tropicamide, and animals were anesthetized with ketamine (50 mg/kg) and xylazine (10 mg/kg) by intraperitoneal injection. Animals were put on the lifting platform in a prostrate state, the grounding electrode was inserted into the subcutaneous tissue at rat's tail root, the reference electrode was placed in rat's mouth, and the test electrode was inserted into the subcutaneous tissue of rat's occipital tuberosity. The resistance of each electrode was checked. Collection of electrophysiological signals began (stimulus frequency 1.3 Hz; frequency band 7.3 Hz) after the requirements were met, fVEP waveform was described by NP wave calibration method, the average value of N2 and P2 was chosen as observation value, and stable waveform of each animal was collected repeatedly for 3 times. SPSS 21.0 statistics software (Chicago, IL) was adopted to conduct statistical analysis of data. The experimental data was expressed with the mean±standard deviation (mean±SEM). Data was analyzed by variance, and the statistical analysis between groups was inspected by One-Way Anova test. $P<0.05$ meant the difference was statistically significant.

Whole retinal patch and Brn3a immunofluorescence staining: 6 rats were selected in random from each group; the right eyeballs were taken out after euthanasia, punctured a few holes at the corneoscleral junction with needle, kept in 4% paraformaldehyde for about 20 min, then the eyeballs were taken out and the cornea and lens were removed. The retina was peeled carefully on an ice surface, cut into a four-leaf shape, and put back to 4% paraformaldehyde to fix for 5 min. The retina was rinsed with 0.01 mol/L phosphate buffer saline (PBS) for 6 min. Blocking solution (Ultra-Cruz® Blocking Reagent, product No.: SC-516214, batch No.: C1317, Santa Cruz Biotechnology, Inc.) was added and shaken on a shaker at room temperature for 2 h, then sucked out. Brn-3a antibody (14A6) was added (product No.: SC-8429, batch No. B1216, Santa Cruz Biotechnology, Inc., used after dilution with diluents at 1:50; diluent: 2.5 mL of blocking solution and 0.15 mL of TritonX-100 were added to 47.35 mL of PBS and mixed well). It was shaken and incubated on a shaker at 2-8° C. for about 72 h. Then it was taken out and balanced till room temperature for 30 min, and then washed with PBS for 5 times. M-IgGκ BP-CFL 488 (product No.: SC-516176, batch No. A1917, Santa Cruz Biotechnology, Inc., used after dilution with diluents at 1:100) was added, shaken and incubated on a shaker at 2-8° C. overnight. It was washed with PBS for 5 times and put on a slide. Then the slide was sealed with mounting medium. A fluorescence microscope was used to observe and evaluate Brn3a-stained positive ganglion cells (Retinal ganglia cells, RGCs). The center of every leaf of the 4-leaf retinal patch was photoed under a 40×confocal microscope, RGCs in every photo by ImageJ bundled with 64-bit Java1.6.0_24 software (dimension selection range: 50-infinity) was counted, and the average value of 4 counts was used as RGC quantity of this animal. SPSS 21.0 statistics software (Chicago, IL) was adopted to conduct statistical analysis of data. $P<0.05$ meant the difference was statistically significant.

Histopathological examination (hematoxylin-eosin staining, HE staining): 6 rats were selected in random from each group, whose eyeballs were collected after euthanasia, put in modified Davidson's solution to fix for 24~72 h, and then transferred to 10% neutral buffering formalin solution. The eyeballs were taken out before HE staining, washed with PBS for three times, and dehydrated with ethanol by gradient (50% ethanol for 90 min, 70% ethanol for 90 min, 85% ethanol for 90 min, 95% ethanol for 60 min, 100% ethanol for 60 min). It was soaked in 1:1 mixture of xylene and ethanol for 1 h, and then soaked in pure xylene for 1 h. Dipping paraffin, embedding and sectioning: The hyalinized tissue was immersed in 1:1 mixture of paraffin and xylene for 90 min, then placed in paraffin for 120 min, and cooled at once. Then, the eyecup specimens at 5 μm were sliced in a row, and baked at 60° C. for future use. The slides were immersed in xylene for 5 min and the procedure was repeated for 3 times. The slides were immersed in ethanol by gradient in turn (100%, 90% and 70%) each for 5 min, and the slides were finally washed with tap water for 5 min. The slides were stained in hematoxylin stain for 5 min. The excess stain on the slides was washed off with water before the 10 s separation of the color with 75% HCl ethanol solution, and the slides were washed with tap water until the micronucleus and nuclear chromatin were clearly detected under a microscope. It was stained with 0.5% eosin solution for 5 min and dehydrated with 70%, 85%, 95% and 100% ethanol in turn for 2 min. It was hyalinized with xylene twice for 1 min each time. The excess xylene around the sections was wiped off (it was noted that they mustn't be in dry), a proper amount of neutral gum was quickly dropwise added and the slides were covered. Pathological sections were observed under an optical microscope, photographed under a 40×optical lens. Each dissection was photographed by selecting two visual fields on the two sides of the optic nerve, then drawn with counting frames of a same size (dimensions of counting frames: L 18.00 cm×W 3.47 cm). RGCs quantity in the counting frames of every photo was counted by 2 persons respectively. The average value of the counts of the 2 persons was considered as the cell quantity on each photo. In the end, the average value of 4 counts of each eye was considered as RGC quantity of this animal. SPSS 21.0 statistics software (Chicago, IL) was adopted to conduct statistical analysis of data. $P<0.05$ meant the difference was statistically significant.

The experimental results were as follows:

1) Effects of AuCs at Different Doses on fVEP of Model Rats

In this experiment, a rat optic nerve injury model was established by a crushing method. The effects of AuCs at different doses on fVEP of SD rats by being administered dropwise to eyes for consecutive 14 days, 3 times a day (dosing interval 5±0.5 h) with 10 μL/eye per time, fVEP were evaluated on Day 7 and Day 14 respectively. After optic nerve was crushed, lower fVEP amplitude, wider waveform and longer latency meant more serious damage.

Figure 15:
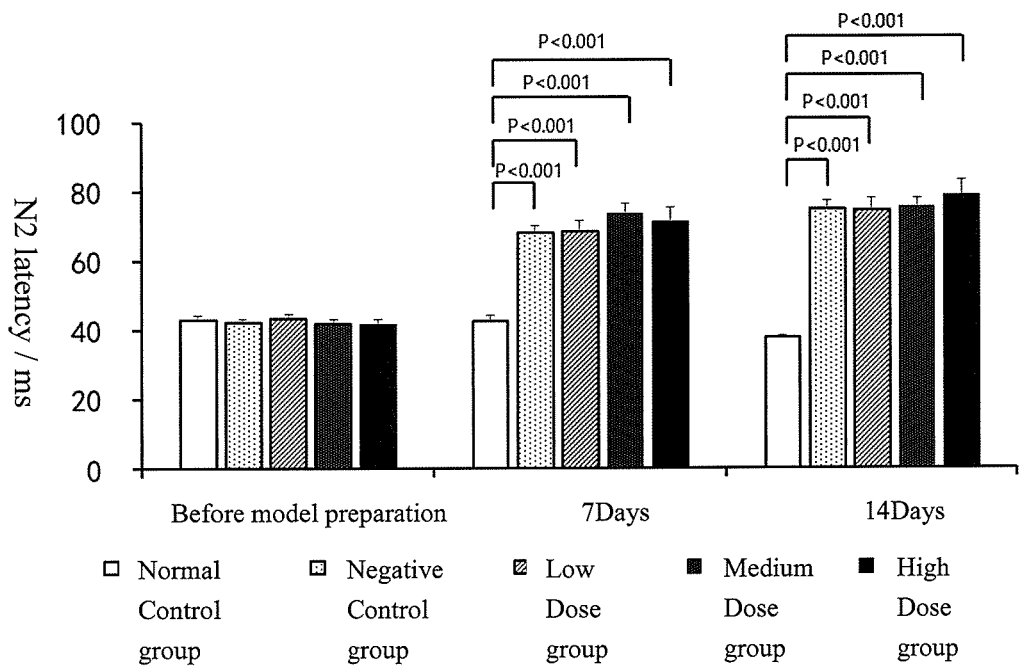
FIG. 15 shows the effect of substances containing AuCs on fVEP N2 latency of rat eyes in the glaucoma model.
Figure 16:
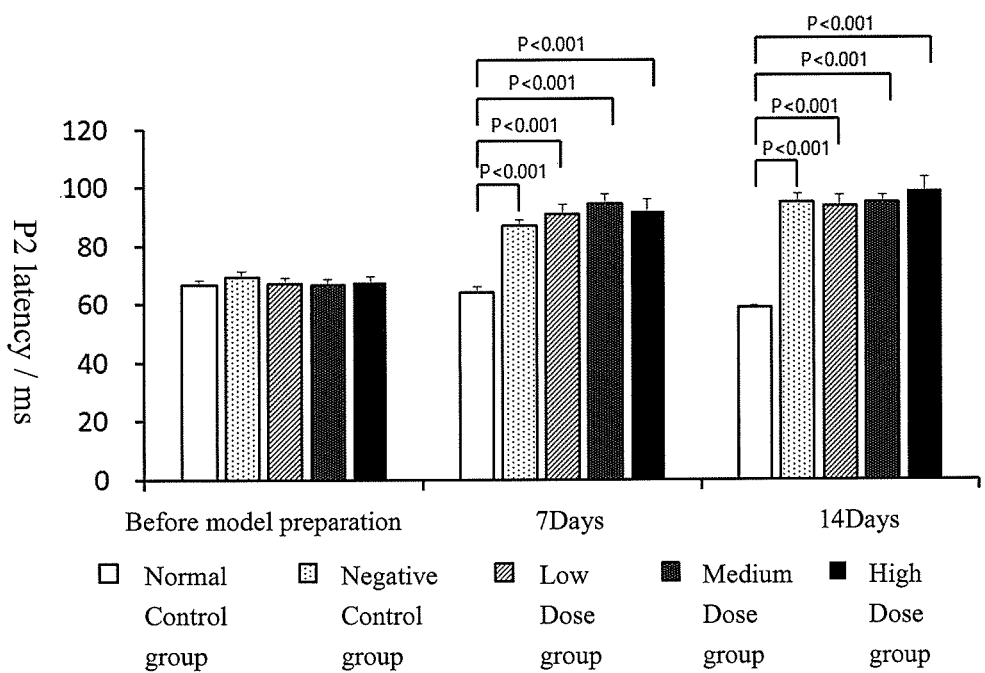
FIG. 16 shows the effect of substances containing AuCs on fVEP P2 latency of rat eyes in the glaucoma model.

N2 and P2 latency: Before model preparation and administration, the animals in the normal control group, negative control group and low, medium and high dose groups did not have significant difference in N2 and P2 latency ($P>0.05$) (FIG. 15 and FIG. 16), which suggested that experiment grouping did not affect the subsequent experiment results. On Day 7 and Day 14 after model preparation and administration, compared with the normal control group, the N2 and P2 latency of the animals in the negative control group and low, medium and high dose groups was lengthened significantly ($P<0.0001$) (FIG. 15 and FIG. 16). It showed that an optic nerve crush rat model was successfully established in this experiment. On Day 7 and Day 14 after model preparation and administration, compared with the negative control group, the N2 and P2 latency of the animals in the low, medium and high dose groups did not have significant difference ($P>0.05$) (refer to FIG. 15 and FIG. 16).

Figure 17:
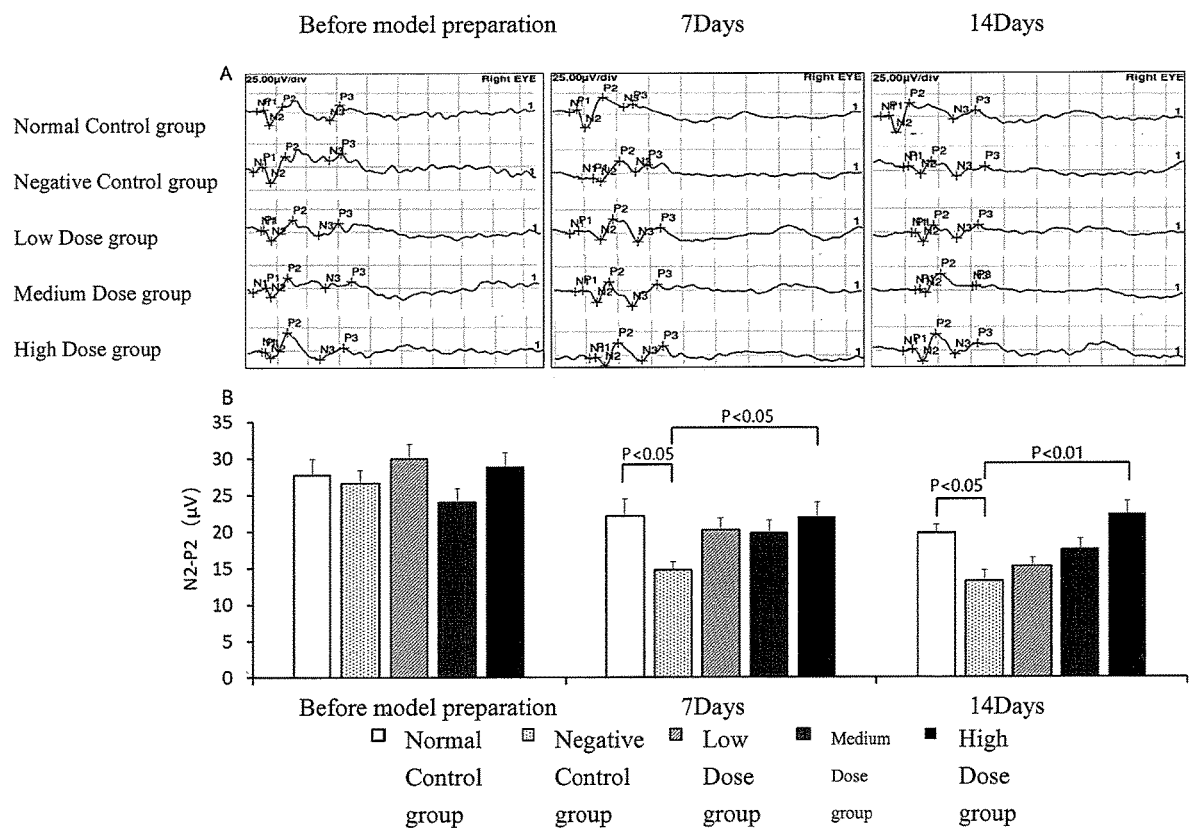
FIG. 17 shows the effect of substances containing AuCs on fVEP N2-P2 amplitude of rat eyes in the glaucoma model.

N2-P2 amplitude: Before model preparation and administration, the animals in the normal control group, negative control group and low, medium and high dose groups did not have significant difference in N2-P2 amplitude ($P>0.05$) (panels A and B of FIG. 17), which suggested that experiment grouping did not affect the subsequent experiment results. On Day 7 after model preparation and administration, compared with the normal control group (22.2±2.3 μV), the N2-P2 amplitude (14.7±1.2 μV) of the negative control group decreased significantly (reduced by 33.7±5.4%, $P<0.05$), which indicated that the visual function and optic nerve of the rats were significantly influenced and an optic nerve crush rat model was prepared successfully in this experiment. Compared with the negative control group, the N2-P2 amplitude (22.0±2.0 μV) of the high dose group increased significantly (up by 49.4±9.1%, $P<0.05$). Compared with the negative control group, the N2-P2 amplitude of the low dose and medium dose groups increased to some extent (low dose group: 20.2±1.6 μV, up by 37.6±7.3%; medium dose group: 29.9±1.5 μV, up by 35.5±6.8%), but they did not have significant difference ($P>0.05$). On Day 14 after model preparation and administration, the N2-P2 amplitude of the negative control group (13.2±1.5 μV) was significantly lower than that of the normal control group (19.7±1.2 μV) (down by 32.9±8.0%, $P<0.05$). Compared with the negative control group, the N2-P2 amplitude (22.4±1.7 μV) of the rat in the high dose group of AuCs increased on a big margin (up by 69.0±8.5%, $P<0.01$), while the low dose and medium dose groups did not have significant effect on improving N2-P2 amplitude (low dose group: 15.2±1.2 μV, up by 14.5±6.2%, $P>0.05$; medium dose group: 17.6±1.4 μV, up by 32.8±7.0%, $P>0.05$). The above result indicated that short-term and long-term administration of AuCs both could significantly increase the N2-P2 amplitude of SD rats and this effect was dose-dependent. Meanwhile, the observation under a microscope found that administration of AuCs could significantly improve the visual field defect caused by the optic nerve crush injury model, which was also dose-dependent. It showed that AuCs had an obvious ameliorative effect on optic nerve injury of animals.

Figure 18:
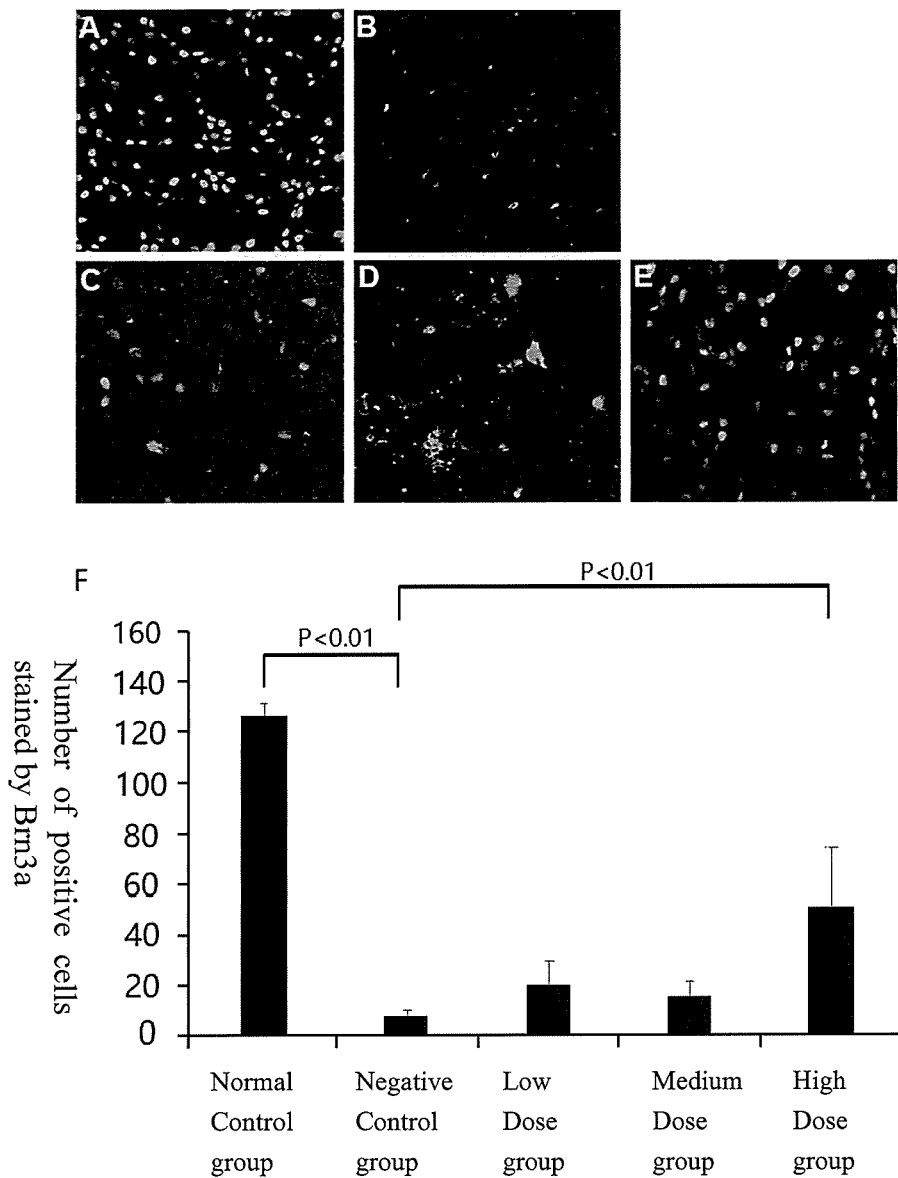
FIG. 18 shows Brn3a staining of animal retina patch and statistical analysis charts of the number of stained positive cells after the substances containing AuCs were administered for 14 consecutive days.

2) Brn3a Immunostaining to Check the Effects of 14 days' Continuous Administration of AuCs at Different Dosages on RGCs of SD Rats Brn3a had an important effect on the survival of neurons, the activation of differentiation-related genes, and the differentiation and survival of RGCs and the extension of axons during rodent retina development. It was an important and highly feasible marker for RGCs. In Brn3a immunostaining, the more Brn3a-positive cells mean survival of more RGCs. The results were shown in FIG. 18. Compared with the normal control group (panel A of FIG. 18) (number of positive cells stained by Brn3a in a single counting frame: 126.5±7.0), the number of Brn3a-positive cells (7.6±1.6) in the negative control group (image B of FIG. 18) was only 6.0±1.3% of that in the normal control group ($P<0.01$) (panel F of FIG. 18), which suggested that after optic nerve crush, a lot of ganglion cells of the animals were lost. Compared with the negative control group, the number of Brn3a-positive cells (50.8±22.9) in the high dose group of AuCs (panel E of FIG. 18) increased significantly (up by 5.6 times, $P<0.01$) (panel F of FIG. 18). Compared with the negative control group, the RGC quantities in the low dose (panel C of FIG. 18) and medium dose group (panel D of FIG. 18) of AuCs increased to some extent (19.6±9.6 and 15.8±5.4 respectively), but they did not have statistical difference ($P>0.05$) (panel F of FIG. 18). The above result supported fVEP experiment results, which suggested that AuCs had an obvious protective effect on the loss of ganglion cells after optic nerve was damaged, and the effect was dose-dependent.

Figure 19:
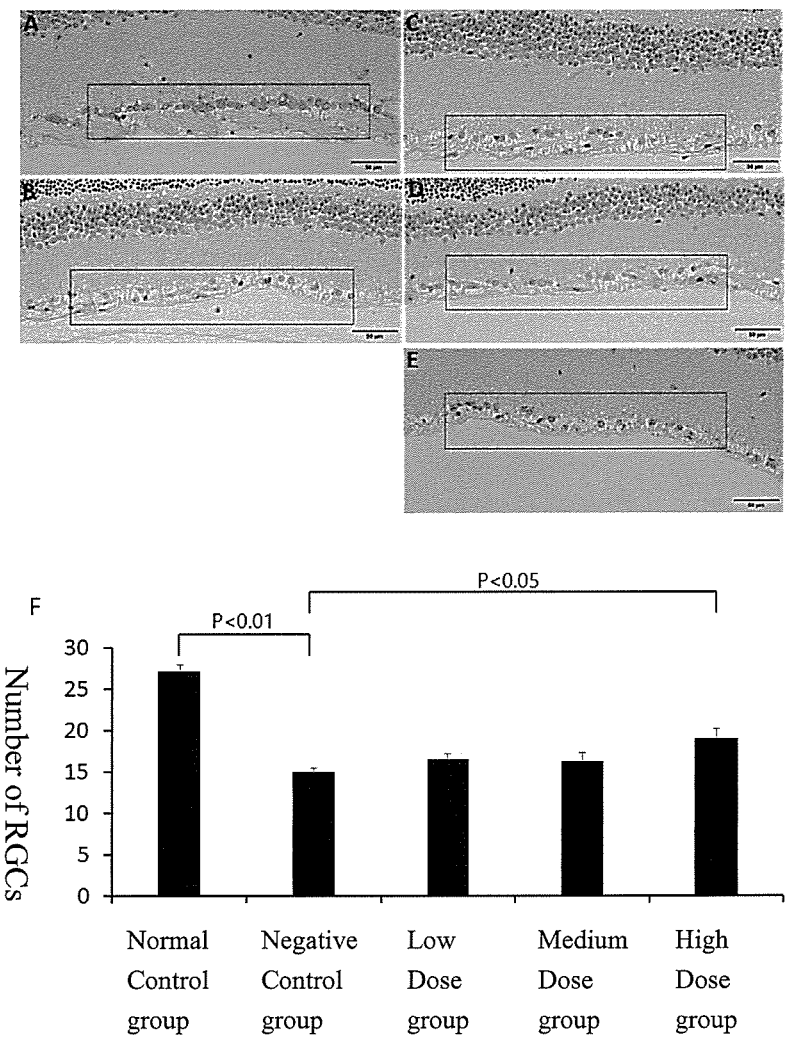
FIG. 19 shows HE staining results of animal retina pathological sections and statistical analysis charts of the number of RGCs after the substances containing AuCs were administered for 14 consecutive days.

3) HE Staining to Check the Effects of 14 Days' Continuous Administration of AuCs at Different Dosages on Retinal Tissue Morphology and RGC Quantity of SD Rats The sections of rat retinal cases were stained with hematoxylin—eosin (hematoxylin-eosin staining, HE staining). In this way, the retinal tissue morphology could be observed from another angle under a microscope and meanwhile the numbers of RGCs were counted. The results were shown in FIG. 19. Compared with the normal control group (panel A of FIG. 19) (number of RGCs in a single counting frame: 27.1±0.9), the retina in the negative control group (panel B of FIG. 19) showed obvious tissue edema with an uneven thickness, loss of RGCs (15.5±0.5, down by 44.8±1.8%, $P<0.01$), and obvious uneven arrangement of RGCs. Compared with the negative control group, the RGC quantity (19.1±1.2) in the high dose group of AuCs (panel E of FIG. 19) increased significantly (up by 27.4±4.4%, $P<0.05$), the retinal tissue structure was improved obviously and tissue edema and vacuolization were reduced obviously. Compared with the negative control group, RGCs quantities of the low dose (panel C of FIG. 19) and medium dose group (panel D of FIG. 19) of AuCs increased to some extent (low dose group: 16.5±0.6, up by 10.4±2.4%; medium dose group 16.2±1.1, up by 8.4±4.1%), but they did not have significant difference ($P>0.05$)) (panel F of FIG. 19). The above result corresponded to the counting result of RGCs immunostained by Brn3a, which suggested that AuCs could reduce RGC loss caused by optic nerve damage, and significantly improved retinal structure and RGCs arrangement, and had a protective effect on optic nerve, which was dose-dependent.

The above result indicated that AuCs could significantly increase fVEP N2-P2 amplitude of the rats in the optic nerve crush injury rat model and significantly reduced the loss of RGCs, had a protective effect against optic nerve damage, visual field defect and RGCs apoptosis, playing a significant role in the improvement of retinal and optic nerve tissue structures and alleviation of visual dysfunction, and could be used as substances containing AuCs to prepare drugs preventing or treating glaucoma.

The AuCs modified with other ligands listed in Table 1 had a similar effect, so they would not be described in details herein.

Embodiment 8: Biosafety Evaluation

1. SH-sy5y Cell Line was Adopted to Evaluate the Biosafety of the Substances containing AuCs at the Cell Level.

Specific method: SH-sy5y cells in the logarithmic growth phase of cells (cells at passage 6) were collected. The concentration of cell suspension was adjusted, and added 1000 μL into each well. The cells were plated, and the cell density was adjusted to 1000-10000 per well. The cell cuture plates (the marginal wells of 96-well plates were filled with cell culture medium) were put in a cell incubator and incubated in a 5% $CO_2$, 37° C. environment for 24 h so that the cells attached to the wall. The 96-well plates were taken out, and then put in a biosafety cabinet after disinfection by alcohol. The original cell culture medium was sucked out, and then solutions of ligand-modified AuCs listed in Table 1 were added, which were diluted with cell culture medium to obtain a final concentration of 1 ppm, 10 ppm, 50 ppm, 100 ppm, 200 ppm and 500 ppm, respectively. An equal volume of fresh cell culture medium was added to the control group (no AuCs). And put it in a cell incubator, and incubated for 48 h. 6 duplicate wells were set for each of the experiment group and the control group. After 48 h of incubation, the culture medium was removed by centrifuging, then washed with PBS for 2-3 times. 100 μL fresh culture medium and 20 μL methyl thiazolyl tetrazolium (MTT) solution (5 mg/ml, i.e., 0.5% MTT) were added to each well, and continued to be cultivated for 4 h. The cultivation was terminated, the 96-well plate was taken out, and centrifuged (1000 r/min) for 10 min. The supernatant was sucked out, and 200 μL DMSO was added to each well, and put on a shaking table, and oscillated at a low speed for 10 min till the color in the wells was uniform and crystal was fully dissolved. The absorbtance of each well was measured at 490 nm by microplate reader. The above operations must be conducted in a sterile environment. Except detection, all the steps were completed in a biosafety cabinet. The experimental supplies were disinfected in an autoclave before use.

Figure 20:
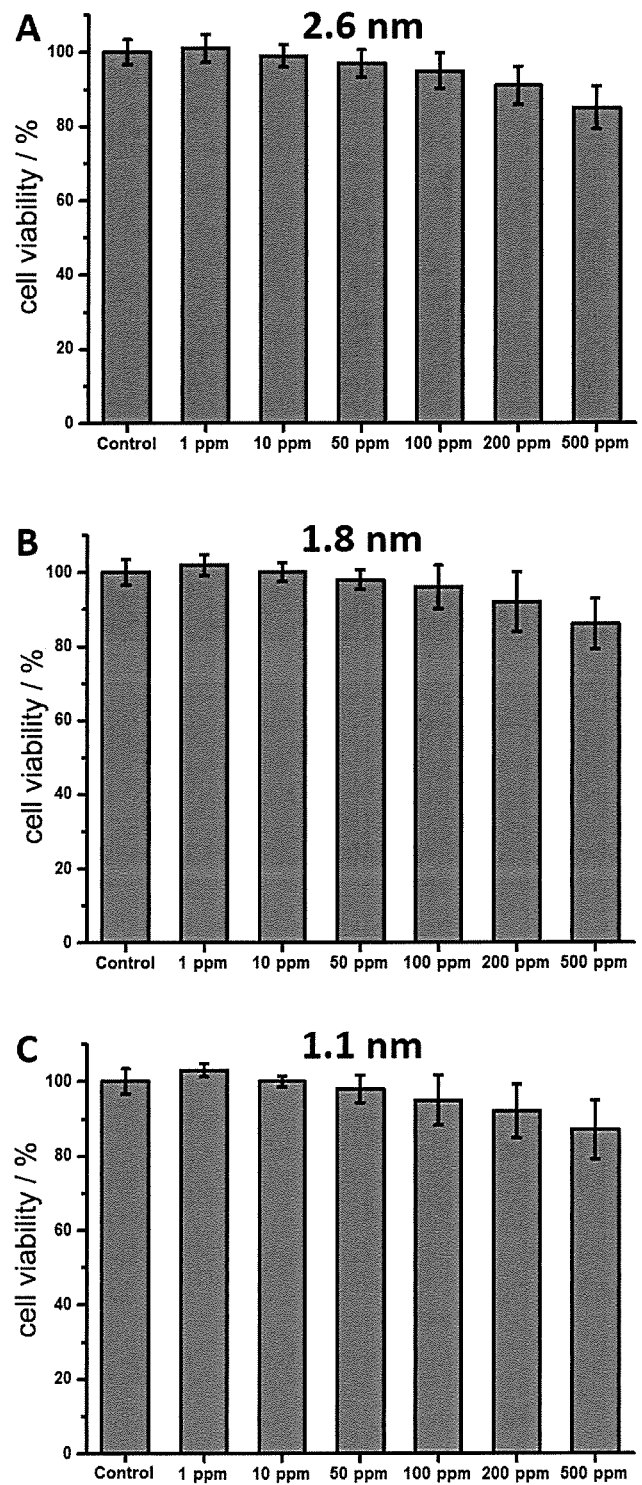
FIG. 20 shows diagrams showing the effect of L-NIBC-modified AuCs of different particle sizes and different concentrations on SH-sy5y neuroblastoma cell viability.

L-NIBC-modified AuCs in Embodiment 2 were taken for example, the results were shown in FIG. 20 where panels A-C showed the effects of AuCs with particle sizes of 2.6 nm, 1.8 nm or 1.1 nm and at final concentrations of 1 ppm, 10 ppm, 50 ppm, 100 ppm, 200 ppm or 500 ppm on SH-sy5y cell viability. It was indicated that at a fairly high concentration (such as: 100 ppm), the addition of L-NIBC-modified AuCs almost did not have any influence on cell viability. At a higher concentration (such as: 200 and 500 ppm), the addition of L-NIBC-modified AuCs would cause slight cell injury (cell death rate is less than 20%). Since 100 ppm was much higher than the lowest effect concentration of the AuCs (0.1 ppm or lower), it could be concluded that L-NIBC-modified AuCs had high safety at the cell level.

Other ligand-modified AuCs with different sizes also had similar effects. They would not be described in detail here.

2. Adopt Mouse Acute Toxicity Study to Evaluate the Acute Toxicity of Substances containing AuCs.

Specific method: For different ligand-modified AuCs listed in Table 1(L-NIBC-modified AuCs with an average diameter of 1.8 nm in Embodiment 2 was taken for example), 60 adult mice were divided into four groups with 15 mice in each group, which were: a control group and three experiment groups. In the control group, mice were fed normally, while in the three experiment groups, mice were fed with AuCs by oral administration (by gavage) at a dose of 0.1 g/Kg body weight, 0.3 g/Kg body weight and 1 g/Kg body weight a day respectively for one week under the condition of normal diet. The mice were fed normally for 30 days after the feeding of AuCs was finished. Abnormal responses of the mice were observed.

In the mice experiment, the ingestion of AuCs with different sizes at three concentrations had no influence on the survival and activity of mice. Even though for high dose intake of 1 g/Kg body weight, the mice remained healthy.

Other ligand-modified AuCs listed in Table 1 also had similar results. They would not be described in details herein. Based on the above results, it could be concluded that AuCs were very safe.

Embodiment 9: Tissues and Metabolic Distribution of AuCs in Mice

Experiment 1:

Operating steps: 80 mice were randomly divided into four groups, 20 mice in each group, and fed with ligand-modified AuCs listed in Table 1 by oral administration (by gavage) at doses of 100 mg/kg, 20 mg/kg, 5 mg/Kg and 1 mg/kg respectively in the groups. After feeding of AuCs, the 20 mice in each group were randomly divided into 4 subgroups with 5 mice in each subgroup. They were sacrificed at the time points of 2 h, 6 h, 24 h and 48 h respectively after feeding. Heart, liver, spleen, lung, kidney and brain tissues were taken separately. Each tissue was weighed, and 2 mL water was added to homogenize, and then 2 mL aqua regia was added and mixed under vortex, and oscillated for 72 h on an oscillator. 2 wt % nitric acid solution was added to a final volume of 10 mL, and centrifuged at 15000 rpm for 15 min. 4 mL of supernatant was sucked, and the content of gold element in the tissue fluid was measured by atomic absorption spectrometry.

The results indicated that AuCs could pass through the blood-brain barrier and reached the brain. They could be excreted out of the body over time, so they did not have obvious accumulation in the body. Therefore, the substances containing AuCs provided in the present invention had a good prospect in the application of preparation of medication treating AD or PD.

Experiment 2:

Operating steps: 80 mice were randomly divided into four groups with 20 mice in each group, and injected intraperitoneally with ligand-modified AuCs listed in Table 1. The doses of AuCs (L-NIBC-modified AuCs with an average diameter of 1.8 nm were taken for example) in each group were 100 ppm, 20 mg ppm, 5 ppm and 1 ppm of mouse body weight respectively. After injection of AuCs, the 20 mice in each group were randomly divided into 4 groups, 5 mice in each group. They were sacrificed at time points of 2 h, 6 h, 24 h and 48 h respectively after administration. Heart, liver, spleen, lung, kidney and brain tissues were taken separately. Each tissue was weighed, and 2 mL water was added to homogenize, then 2 mL aqua regia was added and mixed by vortex, and oscillated for 72 h on an oscillator. 2 wt % nitric acid solution was added to a final volume of 5 mL, and centrifuged at 15000 rpm for 15 min. 1 mL supernatant was sucked, and the content of gold element in the tissue fluid was measured by atomic absorption spectrometry.

Above steps were adopted to carry out experiments for AuCs modified with other ligands listed in Table 1.

The results indicated that after 2 h, the content of gold element in the brain reached 1%-10% of initial concentration. After 6 h, the content in the brain could be maintained at a similar level. After 24 h, the content in the brain decreased significantly. At hour 48 h, the content decreased to near or below the detection limit except for the specimens at a dose of 100 ppm. The above results indicated that substances containing AuCs also had good biosafety at the animal level, which can pass through the blood-brain barrier, and had no obvious accumulation in the body.

In summary, the above experiment results illustrated the following points (the "gold nanoparticles" and "AuCs" mentioned below all refer to the cases with ligand modification):

(1) In the experiment (Embodiment 3) for Aβ aggregation in vitro, it was found that the effect of gold nanoparticles on Aβ aggregation kinetics was related to size. When the particle diameter was greater than or equal to 10.1 nm, the addition of gold nanoparticles could accelerate the aggregation of Aβ, and when the particle size was smaller than or equal to 6.0 nm, the aggregation of Aβ was inhibited, but complete inhibition of Aβ aggregation could not be achieved. However, when AuCs were used (average diameter is less than 3 nm), all the AuCs could significantly inhibit Aβ aggregation in vitro, and this effect was related to the concentration of AuCs. When the concentration of AuCs reached 5-10 ppm, the aggregation of Aβ could be inhibited completely, and the minimum concentration required for complete inhibition was related to the type of ligand and the diameter of AuCs.

(2) In the RGC-5 optic ganglion cell injury model experiment (Embodiment 4-Embodiment 6), it was found that AuCs modified with different ligands and in different sizes (the average diameter was smaller than 3 nm) in the present invention, could significantly increase cell viability of the RGC-5 injury model, which suggested that AuCs had significant efficacy at cell level. In comparison, the gold nanoparticles in a larger size did not have a significant effect or did not have an effect. As none of the ligands had an effect on Aβ aggregation and different RGC-5 optic ganglion cell injury model (Embodiment 3-Embodiment 6), it could be concluded that the efficacy of AuCs was from AuCs themselves. It offered a new approach to the application of AuCs.

(3) Further, the present invention adopted rat glaucoma optic nerve clamping injury model (Embodiment 7) to further verify the efficacy of AuCs which indicated that the AuCs could significantly increased the N2-P2 amplitude of fVEP of the rats in the optic nerve crush injury model and significantly reduced the loss of RGCs, had an obvious protective effect against optic nerve damage, visual field defect and RGCs apoptosis, played an obvious role in the improvement of the structure and arrangement of retinal cells. It indicated that AuCs could alleviate glaucoma-related visual dysfunction and could be used to prepare drugs preventing and/or treating related diseases.

(4) In the experiment for further evaluation of biosafety (Embodiment 8), when AuCs at a concentration of 100 ppm by weight (the following ppm referred to weight percentage) were co-cultured with nerve cells, they did not have an obvious influence on the viability of cells; when the concentration exceeded 100 ppm (much higher than the lowest effect concentration of the AuCs), the cell viability decreased slightly. As the lowest effect concentration of AuCs (0.1-1 ppm) was much lower than 100 ppm, it could be concluded that AuCs had excellent biosafety at the cell level. In the mouse acute toxicity test, it had been found that a dose of 1 g/Kg body weight (equivalent to 1000 ppm) AuCs administered once a day for seven days consecutively did not cause adverse effect. In the study of in vivo distribution and pharmacokinetics in mice (Embodiment 9), the content of gold element in the brain reached 1%-10% of the initial concentration after 2 h. After 6 h, the content in the brain maintained at a similar level. After 24 h, the content in the brain decreased significantly. At 48 h, the content decreased to below the detection limit except for the specimens at a dose of 100 ppm. The above results indicate that a substance containing AuCs also has good biosafety at the animal level, could pass through the blood-brain barrier, and has no obvious accumulation in the body, so it had a good prospect in the application in preparation of medication treating glaucoma.

(5) Compared with current technology, the ligands used in the present invention were not specifically designed for the aggregation behaviors of Aβ, and the contrast experiment indicated that the ligands used had no obvious effect on the aggregation of Aβ (Embodiment 3). But since the size of AuCs was smaller than the size of Aβ protein itself, the aggregation of Aβ could be greatly inhibited by the combination of the size effect and the weak molecular interactions. The excellent efficacies in RGC-5 optic ganglion cell injury model and rat glaucoma optic nerve clamping injury model further confirmed the feasibility of AuCs in the preparation of medication for preventing or treating of glaucoma.

INDUSTRIAL APPLICABILITY

The present invention provides the application of substances containing AuCs in the preparation of drugs preventing and/or treating glaucoma. The substances containing AuCs can significantly reduce the loss of RGCs of the rats in the glaucoma optic nerve crush injury rat model, and have an obvious protective effect on optic nerve damage, and can narrow visual field defect and reduce RGC apoptosis, and play a significant role in the improvement of retinal and optic nerve tissue structures and alleviation of visual dysfunction, and have good biocompatibility at the animal level, and can be used as new drugs preventing and/or treating glaucoma. They are suitable for industrial application.

The invention claimed is:

1. A method for treating a subject with glaucoma, said method comprising:
    administrating a pharmaceutical composition into the subject with glaucoma;
    wherein said pharmaceutical composition comprises:
        a substance containing gold clusters (AuCs); and
        a pharmaceutically acceptable excipient;
        wherein the AuCs have a gold core with a diameter smaller than 3 nm, and a ligand Y coating the gold core externally.

2. The method of claim 1, wherein the diameter of the gold core is 0.5-2.6 nm.

3. The method of claim 1, wherein the ligand Y is one selected from the group consisting of L(D)-cysteine and its derivatives, cysteine-containing oligopeptides and their derivatives, and other thiol-containing compounds.

4. The method of claim 3, wherein the L(D)-cysteine and its derivatives are selected from the group consisting of L(D)-cysteine, N-isobutyryl-L(D)-cysteine (L(D)-NIBC) or N-acetyl-L(D)-cysteine (L(D)-NAC).

5. The method of claim 3, wherein the oligopeptides containing cysteine and their derivatives are selected from the group consisting of L-arginine-L-cysteine (RC), L-cysteine-L-arginine (CR), L-cysteine-L-histidine dipeptide (CH), L-histidine-L-cysteine dipeptide (HC), L-glutathione (GSH), L-lysine-L-cysteine-L-proline tripeptide (KCP), L-proline-L-cysteine-L-arginine tripeptide (PCR), glycine-L-cysteine-L-arginine tripeptide (GCR), glycine-L-serine-L-cysteine-L-arginine tetrapeptide (GSCR), and glycine-L-cysteine-L-serine-L-arginine tetrapeptide (GCSR).

6. The method of claim 3, wherein other compounds containing thiol are selected from the group consisting of 1-[(2S)-2-methyl-3-thiol-1-oxopropyl]-L-proline (Cap), thioglycollic acid, mercaptoethanol, thiophenol, D-3-trolovol, N-(2-mercaptopropionyl)-glycine, and dodecyl mercaptan.

* * * * *